(12) United States Patent
Decout et al.

(10) Patent No.: US 7,772,198 B2
(45) Date of Patent: Aug. 10, 2010

(54) CFTR CHANNEL MODULATORS

(75) Inventors: Jean-Luc Decout, Vaulnaveys le Haut (FR); Christel Routaboul, Saint Martin d'Heres (FR); Frederic Becq, Saint Benoit (FR); Caroline Norez, Poitiers (FR)

(73) Assignees: Centre National de la Recherche Scientifique, Paris (FR); Universite Joseph Fourier, Grenoble (FR); Universite de Poitiers, Poitiers (FR)

( * ) Notice: Subject to any disclaimer, the term of this patent is extended or adjusted under 35 U.S.C. 154(b) by 1072 days.

(21) Appl. No.: 11/408,911

(22) Filed: Apr. 21, 2006

(65) Prior Publication Data

US 2006/0258612 A1 Nov. 16, 2006

Related U.S. Application Data

(63) Continuation-in-part of application No. PCT/FR2004/050528, filed on Oct. 21, 2004.

(30) Foreign Application Priority Data

Oct. 23, 2003 (FR) .................................. 03 12417

(51) Int. Cl.
| | |
|---|---|
| A61K 31/70 | (2006.01) |
| A61K 31/675 | (2006.01) |
| A61K 31/519 | (2006.01) |
| A01N 43/90 | (2006.01) |
| C07H 19/00 | (2006.01) |
| C07H 19/167 | (2006.01) |
| C07H 19/173 | (2006.01) |
| C07D 487/00 | (2006.01) |
| C07D 211/82 | (2006.01) |
| C07D 213/06 | (2006.01) |

(52) U.S. Cl. .......................... 514/43; 514/45; 514/46; 514/86; 514/89; 514/262.1; 536/27.11; 536/27.62; 536/27.81; 544/262; 546/348

(58) Field of Classification Search ........................ None
See application file for complete search history.

(56) References Cited

U.S. PATENT DOCUMENTS

| | | | | |
|---|---|---|---|---|
| 5,516,798 | A * | 5/1996 | Ferket | 514/556 |
| 7,175,850 | B2 * | 2/2007 | Cevc | 424/401 |
| 7,417,147 | B2 * | 8/2008 | Bodor | 546/91 |
| 2004/0219160 | A1 * | 11/2004 | Tzianabos et al. | 424/184.1 |
| 2008/0269190 | A1 * | 10/2008 | Husfeld et al. | 514/210.17 |

OTHER PUBLICATIONS (R) Vorkman et al., "CFTR Chloride Channel Drug Discovery—Inhibitors as Antidiaharrheals and Activators for Therapy of Cystic Fibrosis," Current Pharmaceutical Design, 12, 2235-2247 (2006): supplied by applicant.*

Al-Awqati, Qais, "Alternative treatment for secretory diarrhea revealed in a new class of CFTR inhibitors", *J. Clin. Invest.*, vol. 110, pp. 1599-1601 (2002).
Akabas, Myles H., "Cystic Fibrosis Transmembrane Conductance Regulator", *The Journal of Biological Chemistry*, vol. 275(6), pp. 3729-3732 (2000).
Sheppard et al., "Structure and Function of the CFTR Chloride Channel", *Physiological Reviews*, vol. 79 (Suppl. 1), pp. S23-S45 (1999).
Ma et al., "Thiazolidinone CFTR inhibitor identified by high-throughput screening blocks cholera toxin-induced intestinal fluid secretion", *J. Clin. Invest.*, vol. 110, pp. 1651-1658 (2002).
Ma et al., "High-affinity Activators of Cystic Fibrosis Transmembrane Conductance Regulator (CFTR) Chloride Conductance Identified by High-throughput Screening", *The Journal of Biological Chemistry*, vol. 227(40), pp. 37235-37241 (2002).
Routaboul et al., "New stereoselective reaction of methylglyoxal with 2-aminopyridine and adenine derivatives: Formation of imino acid-nucleic base derivatives in water under mild conditions", *Chem. Commun.*, pp. 1114-1115 (2002).
Oya et al., "Methylglyoxal Modification of Protein", *The Journal of Biological Chemistry*, vol. 274(26), pp. 18492-18502 (1999).
Ermolinsky et al., "Dinucleoside Monophosphates Containing AZT and 1-Methyladenosine or 7-Methylguanosine", *Nucleosides, Nucleotides & Nucleic Acids*, vol. 22 (5-8), pp. 853-855 (2003).
Hume et al., "Anion Transport in Heart", *Physiological Reviews*, vol. 80(1), pp. 31-81 (2000).

* cited by examiner

*Primary Examiner*—Lawrence E Crane
(74) *Attorney, Agent, or Firm*—Heslin Rothenberg Farley & Mesiti PC

(57) ABSTRACT

The invention concerns pharmaceutical formulas designed for the treatment of diseases related to CFTR channel dysfunction, such as cystic fibrosis, asthma or diarrhoea. These formulas contain a molecule, coming in the form of a zwitterion at physiological pH, with the general formula:

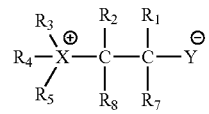

where X=N or P; and
Y=O or S.

A representative example is:

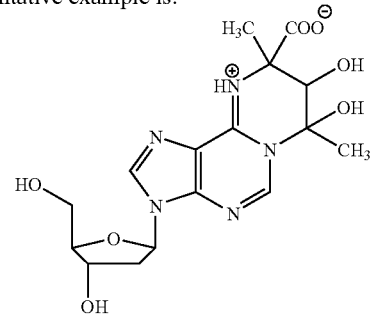

6 Claims, 2 Drawing Sheets

CFTR CHANNEL MODULATORS

CROSS-REFERENCE TO RELATED APPLICATIONS

This application is a Continuation-in-Part application of PCT Application Serial Number PCT/FR2004/050528, filed Oct. 21, 2004, published in French on May 6, 2005, Publication Number WO 2005/039589, which PCT application claims priority from French application FR 0312417, filed Oct. 23, 2003, which are hereby incorporated by reference in their entirety.

FIELD OF THE INVENTION

The invention concerns pharmaceutical formulas for use in the treatment of diseases related to CFTR channel dysfunctions such as cystic fibrosis, asthma or diarrhoea. These formulas contain a molecule which, at physiological pH, comes in the form of a zwitterion with the formula:

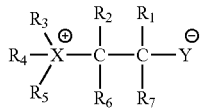

where X=N or P;
Y=O or S;
$R_1$ to $R_7$ represent: —, H, or carbon chains, substituted or not, which may contain heteroatoms;

except for betaine.

BACKGROUND OF THE INVENTION

The CFTR protein, or "cystic fibrosis transmembrane conductance regulator" protein, is a transmembrane protein brought to light during research on the gene responsible for cystic fibrosis (or mucoviscidosis). The CFTR channel appears to be one of the keys to the regulation of chloride ion transport in epithelial cells. Epithelia form a continuous barrier between the outside environment and the internal medium while allowing the transport of ions, solutes and macromolecules between these compartments. The absorption of $Na^+$ and the secretion of $Cl^-$ are major elements in the epithelial function.

Chloride ions penetrate into the epithelial cell through the basolateral surface with the help of a cotransporter, in the form of ($Na^+$, $K^+$, $2 Cl^-$) and leave it using the CFTR channels of the apical surface. [Al-Awqati, Q. (2002). Alternative treatment for secretory diarrhea revealed in a new class of CFTR inhibitors. J Clin Invest 110, 1599-1601].

Two types of pathologies can be associated with opposing CFTR channel dysfunctions.

Inhibition of the function is responsible for problems linked to cystic fibrosis. In this disease, due to genetic mutations, either the CFTR protein encoded is not delivered to the apical surface, or it cannot be activated, whence an impossibility for the chloride ions to leave the epithelial cell. This phenomenon induces absorption of sodium ions and leads to the thickening of mucus, obstructing the respiratory tract.

Inversely, overactivity of the CFTR channel causes diarrhoea. Excessive elimination of salts is accompanied by a loss of water, and therefore problems linked to dehydration. Overactivity of the CFTR channels can follow the presences of the toxins from bacteria such as *Escherichia coli* or *Vibrio cholerae*.

The CFTR protein is a member of the superfamily of ABC (ATP-Binding Cassettes) transporters. It is made up of 1480 amino acids [Akabas, M. H. (2000). Cystic fibrosis transmembrane conductance regulator. Structure and function of an epithelial chloride channel. J Biol Chem 275, 3729-3732; Hume, J. R., Duan, D., Collier, M. L., Yamazaki, J., and Horowitz, B. (2000). Anion transport in heart. Physiol Rev 80, 31-81; Sheppard, D. N., and Welsh, M. J. (1999). Structure and function of the CFTR chloride channel. Physiol Rev 79, S23-45] comprising two homologous parts linked together by a cytoplasmic regulator domain (R). Each part has six transmembrane domains (M1 to M6 and M7 to M12) and a nucleotide binding domain (NBD-1 and NBD-2). There are two N-glycosylated sites between transmembrane domains M7 and M8.

The twelve transmembrane domains form a channel whose activity is determined by the phosphorylation of the R domain, as well as by the hydrolysis of ATP molecules bound in the NBDs. Anions and cations are present in the extracellular cone. The selectivity of this channel for anions seems mainly to be due to the presence of an arginine residue, Arg-352 (R352), at the tip of the cytoplasmic cone. The minimum diameter of this pore is approximately 5.3 Å. This size was determined using the largest anions which can penetrate into the cell. Transiently, however, the channel can dilate up to 13 Å in diameter.

The various CFTR channel activators known to date act in different ways. Among others, three modes of action can be mentioned:

those which act directly on the NBDs: genistein, which extends the opening of the channel; NS-004 or MPBs (substituted benzo[c]quinolizinium);

those which act by increasing the quantity of cyclic AMP needed to activate the R regulator domain: forskolin, which activates the cyclic AMP biosynthesis; milrinone, thought to act through its phosphodiesterase inhibiting action;

those which inhibit proteine phosphatase, enzymes which regulate the closing of the channel by dephosphorylation of the R domain, i.e. bromotetramisole or certain xanthines.

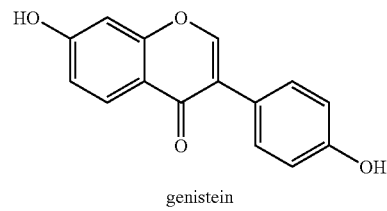
genistein

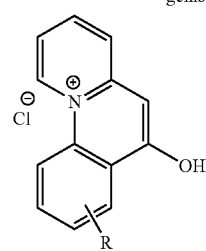
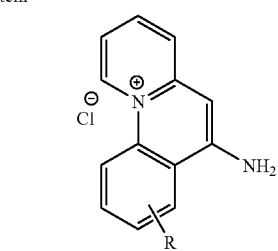
MPB

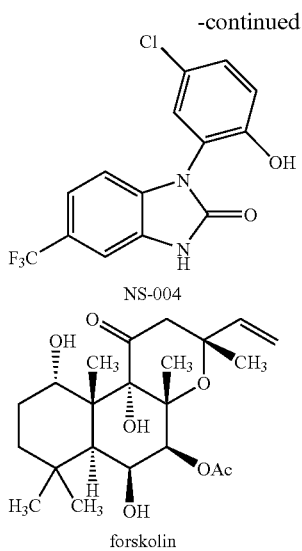
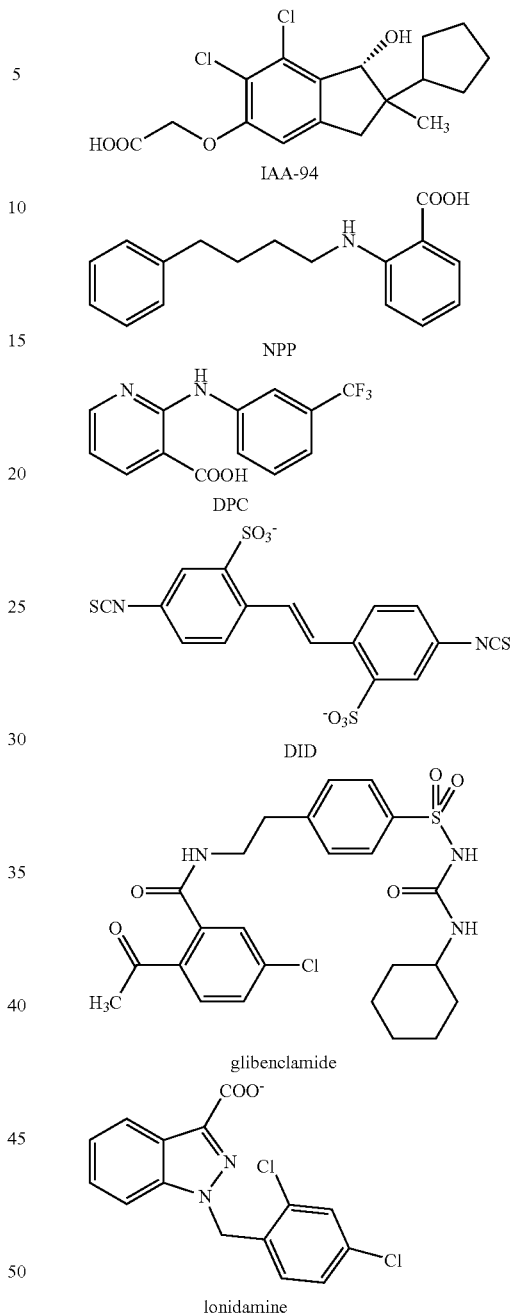

As for the CFTR channel inhibitors, their mode of action usually consists in blocking the pore, thus keeping the ions from crossing through the channel [Hume, J. R., Duan, D., Collier, M. L., Yamazaki, J., and Horowitz, B. (2000). Anion transport in heart. Physiol Rev 80, 31-81]. Among others, we can mention carboxylic acids such as IAA-94 (indanyloxy-acetic acid), DPC (diphenylamine-2-carboxylate) and NPPB (5-nitro-2-(3-phenylpropylamino)benzoate), DIDS (4,4'-di-isothiocyanostylbene-2,2'-disulphonic acid) or sulphony-lureas, including glibenclamine:

In high concentrations, these molecules inhibit the CFTR channels and are not specific to these channels. A 58-µM concentration of lonidamine is needed to inhibit 50% of the activity of the CFTR channel (IC50). These inhibitors also act on the other chloride channels and the potassium channels.

In 2002, Ma et al. reported a new class of inhibitors and new families of activators, both with very strong activity compared to those previously observed [Ma, T., Thiagarajah, J. R., Yang, H., Sonawane, N. D., Folli, C., Galietta, L. J., and Verkman, A. S. (2002a). Thiazolidinone CFTR inhibitor identified by high-throughput screening blocks cholera toxin-induced intestinal fluid secretion. J Clin Invest 110, 1651-1658; Ma, T., Vetrivel, L., Yang, H., Pedemonte, N., Zegarra-Moran, O., Galietta, L. J., and Verkman, A. S. (2002b). High-affinity activators of cystic fibrosis transmembrane conductance regulator (CFTR) chloride conductance identified by high-throughput screening. J Biol Chem 277, 37235-37241]:

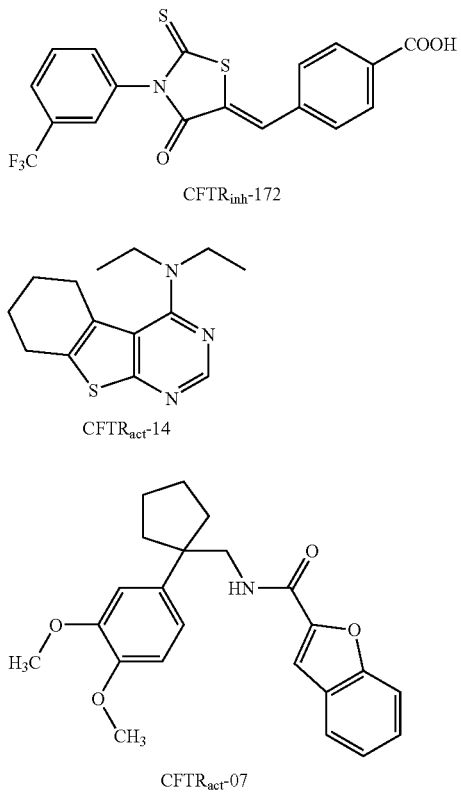

SUMMARY OF THE INVENTION

These new inhibitors are of the 2-thiooxo-4-thiazolidinone type. They have specific activity for CFTR. One of them, CFTR$_{inh}$-172 presents 50% inhibition (IC50) for a 0.2-μM concentration as well as an absence of toxicity at 7 days in mice for a 10 mg/kg injection. It thus has the necessary advantages for therapeutic application. A dose injected in mice (250 μg/kg) reduces diarrhoea caused by the cholera toxin by more than 90% for 6 hours.

As for the new activators, they were discovered by screening a collection of 60,000 compounds. Some of them have proven to be specific to CFTR and are particularly effective, with a concentration needed to obtain 50% of maximum activity (EC50) lower than 200 nM, as well as an absence of toxicity on cells after 24 hours of incubation. Among these derivatives, we should mention the presence of heterocyclic compounds such as CFTR$_{act}$-07 and CFTR$_{act}$-14.

Despite the discovery of these promising molecules and the arsenal already in place, there is a real need to develop molecules which modulate CFTR channel functions and that have a specificity, an effectiveness and an absence of toxicity that are suited to therapeutic applications.

In this invention, the Applicants have demonstrated that molecules which, at physiological pH, come in the form of a zwitterion with a well-determined formula, had such activity and such properties.

The invention thus concerns the use of a molecule which, at physiological pH, comes in the form of a zwitterion with the formula:

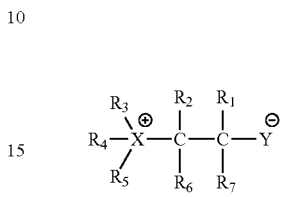

where X=N or P;
Y=O or S;
R$_1$ to R$_7$ represent: —, H, or carbon chains, substituted or not, which may contain heteroatoms;

except for betaine, for preparing a medicinal product designed to treat diseases related to CFTR channel dysfunction.

DETAILED DESCRIPTION OF THE INVENTION

Figure 1:
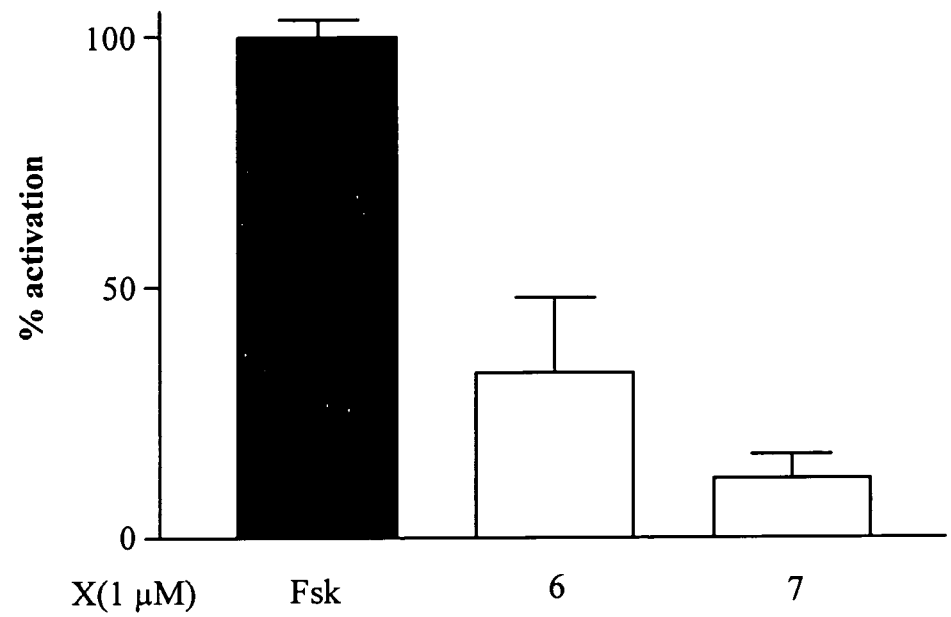
FIG. 1: Effect of the compounds of the invention (compounds 1 to 4, 6 to 7 and 9 to 10), at a concentration of 1 μM, on the CFTR receptor overexpressed in CHO-WT cells. The 100% activation reference corresponds to the activation observed in the presence of 1 μM of forskolin.
Figure 1:
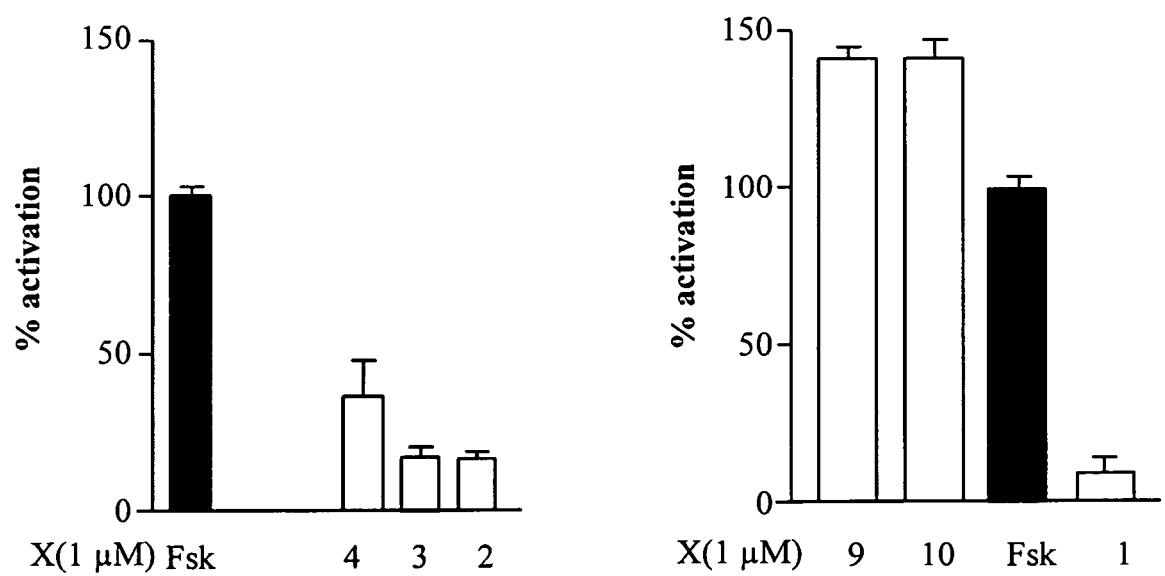

The molecules concerned by this therapeutic application are thus characterised by their biological activity, in this case their ability to modulate CFTR channel functions. Moreover, therapeutic use of these molecules is guaranteed by their non-toxicity.

By CFTR channels is meant both the isolated human channel and all the variants containing mutations. This notably includes proteins of other animal species, as well as naturally mutated proteins. A major category of mutated human CFTR channels concerns the forms found in cystic fibrosis, notably ΔF508 mutants (deletion of a phenylalanine in position 508) and G551D (replacement of a glycine residue by an aspartic acid in position 551).

These molecules can have an inhibitor or activator effect on the CFTR chloride channels. Their action is specific to this type of channel, in other words these molecules have little or no activity on other ion channels (other chloride channels, potassium channels, etc.).

Activators will have a beneficial effect on the mutated channels responsible for cystic fibrosis. In the case of non-mutated channels, the activating molecules will have bronchodilating properties that are beneficial in the case of many obstructive respiratory diseases, such as asthma.

On the other hand, the inhibitors will be used in the case of diarrhoea caused, for example, by the bacillus responsible for cholera.

Betaine is excluded from the molecules concerned by the invention insofar as document U.S. Pat. No. 5,516,798 has already disclosed its use in treating diarrhoea. However, the mechanism of action was absolutely not elucidated in this document and no general formula for the active molecules can be deduced from it.

In this invention, the term "physiological pH" refers to the pH of the body of the organism to be treated, and more especially the pH near the molecule's site of action according to the invention, i.e. in the environment of the targeted CFTR channel. In practice, this means a pH between 5 and 9, preferably between 6 and 8, notably a pH of 7.4.

The molecule according to the invention comes in the form of a zwitterion at said pH. A zwitterion is defined as an entity that has both a positive charge and a negative charge.

Under the particular conditions of the invention, the positive charge is on a nitrogen ($N^+$) or phosphorus ($P^+$) atom, while the negative charge is linked to the presence of a deprotonated carboxylate, hydroxyl or thiol function ($O^-$ or $S^-$), the two atoms having these opposite charges being separated by two carbon atoms.

While the molecule used in the claim comes in the form of a zwitterion at physiological pH, it may, on the other hand, be prepared and/or delivered in a non-zwitterionic form, notably in another acid-base form.

In the definition of the molecules concerned by claim 1, the fact that $R_1$ to $R_7$ may represent "—" means that the atom adjacent to R has at least one double bond, as illustrated below:

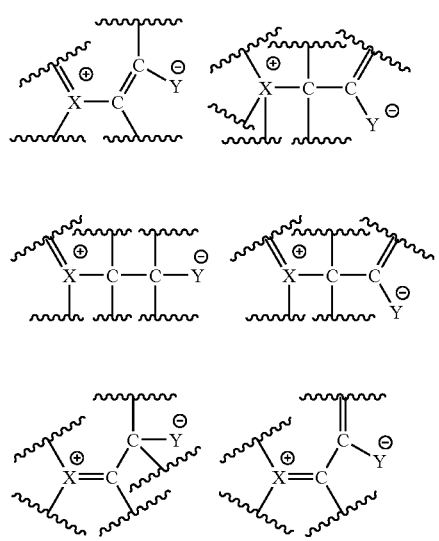

The Applicants have demonstrated that the presence of at least one ring in the molecules defined in claim 1 was advantageous within the framework of the invention. Consequently, in a preferred embodiment, $R_1$ and/or $R_2$ and/or $R_3$ and/or $R_4$ and/or $R_5$ and/or $R_6$ and/or $R_7$ form an aromatic or non-aromatic ring. It should be pointed out that this definition excludes betaine. There are many possibilities, notably:

- the X atom is included in one or two aromatic or non-aromatic rings;
- the Y atom is borne by or substitutes for an aromatic or non-aromatic ring;
- the X atom is included in one or two aromatic or non-aromatic rings and the Y atom is borne by an aromatic or non-aromatic ring;
- the X atom is included in one or two aromatic or non-aromatic rings and the Y atom is borne by one of the aromatic or non-aromatic rings including the X atom.

In this context, a first family of molecules that can be used according to the invention has the following formula:

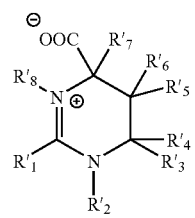

where $R'_1$ to $R'_8$ represent: —, H, or carbon chains, substituted or not, which may contain heteroatoms;

$R'_1$ and $R'_2$ may form an aromatic or non-aromatic ring.

Preferably, the molecules have:

$R'_4 = R'_5 = OH$;
$R'_6 = R'_8 = H$;

and advantageously:

$R'_3 = R'_7 = CH_3$.

The positive charge is borne by the imine function, while the negative charge is linked to the presence of a carboxylate group.

The synthesis method for certain molecules in this family is described in Routaboul et al. (2002) [Routaboul, C., Dumas, L., Gautier-Luneau, I., Vergne, J., Maurel, M. C., and Décout, J. L. (2002). New stereoselective reaction of methylglyoxal with 2 aminopyridine and adenine derivatives: Formation of imino acid-nucleic base derivatives in water under mild conditions. Chem Commun, 1114-1115]. This document specifically describes the reaction between two molecules of methylglyoxal and 2-aminopyridine, or adenine, or adenosine, or 2'-deoxyadenosine, or 9-propyladenine, or cytosine or polyadenylic acid (polyA). An analogous reaction between methylglyoxal and the arginine residue of the proteins (arginine or its protected derivatives on the α-amino acid group) has already been reported [Oya, T., Hattori, N., Mizuno, Y., Miyata, S., Maeda, S., Osawa, T., and Uchida, K. (1999). Methylglyoxal modification of protein. Chemical and immunochemical characterization of methylglyoxal-arginine adducts. J Biol Chem 274, 18492 18502]. These previously disclosed adducts are represented below:

| α-ketoaldehyde + X (diazotized derivatives whose N atoms are separated by a C atom, or amidines in the widest sense of the term) | Adducts (compounds of bis-addition of aldehyde, or cyclic α-iminoacids) of X: |
|---|---|
| methylglyoxal + 2-aminopyridine | 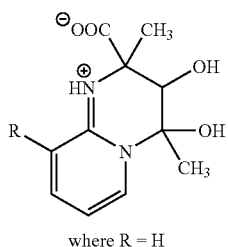<br>where R = H |
| methylglyoxal + adenine | 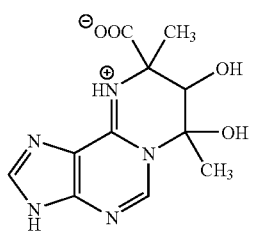 |
| methylglyoxal + adenosine | 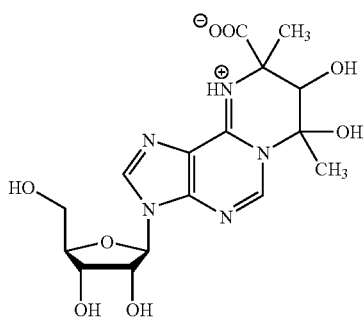 |
| methylglyoxal + 2'-deoxyadenosine | 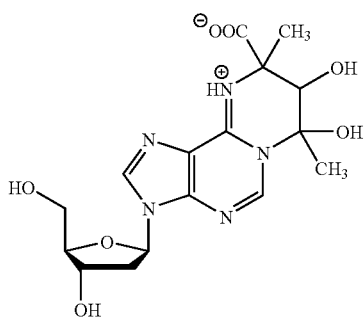 |
| methylglyoxal + 9-propyladenine | 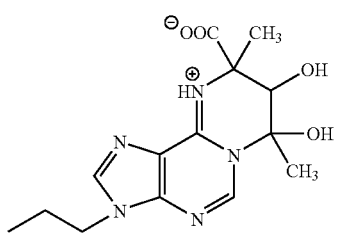 |

| α-ketoaldehyde + X (diazotized derivatives whose N atoms are separated by a C atom, or amidines in the widest sense of the term) | Adducts (compounds of bis-addition of aldehyde, or cyclic α-iminoacids) of X: |
|---|---|
| methylglyoxal + cytosine | 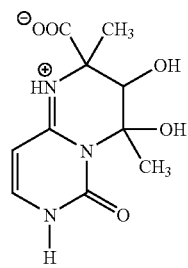 |
| methylglyoxal + polyadenylic acid (polyA) | 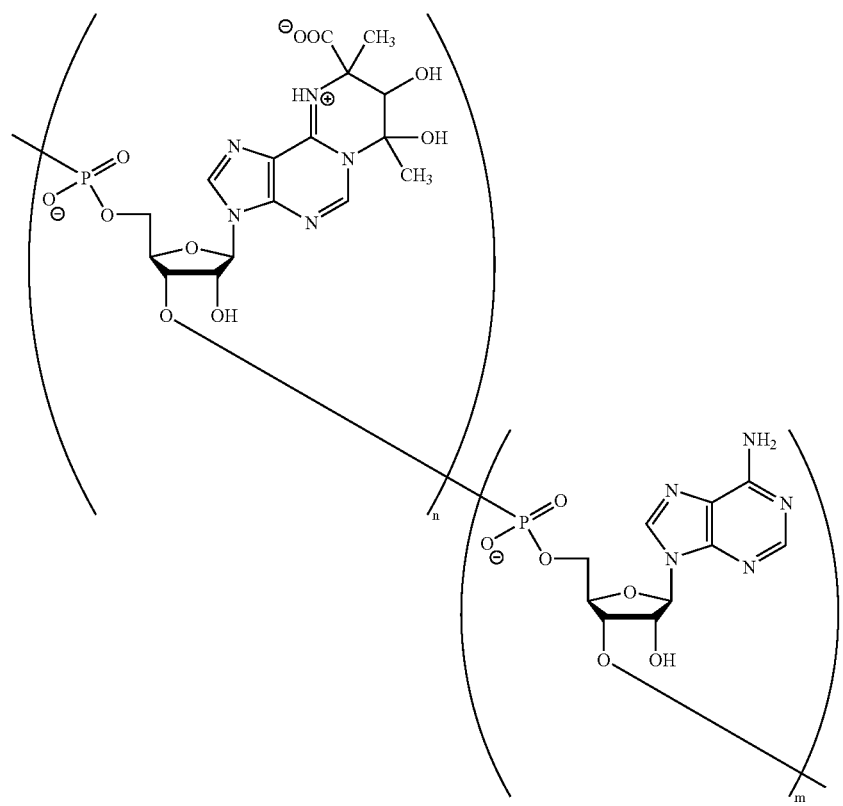 |
| methylglyoxal + arginine an its derivatives (R) | 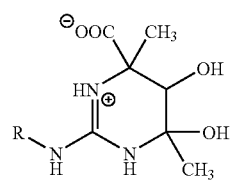 |

On the other hand, no biological activity had been reported for these molecules. The Applicants have observed that compounds with such a formula were CFTR channel activity modulators and that, consequently, these compounds could be used therapeutically in the context of the invention.

Moreover, the Applicants have developed new molecules on the basis of this same reaction. More precisely, these new adducts were obtained through the condensation of 2 α-ketoaldehyde molecules possessing enolisable hydrogen atoms on a molecule with two nitrogen atoms separated by a carbon which are able to react with α-ketoaldehyde, in the presence of $H_2O$ and/or an organic solvent such as ethanol, at a pH of 1 to 10 and a temperature between 25° C. and 80° C. This reaction gives rise to α-iminoacids, with the following formula at physiological pH:

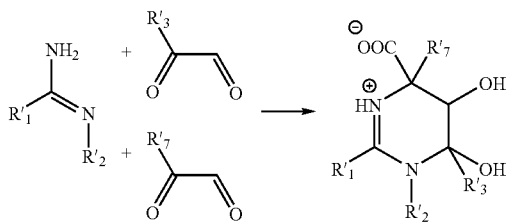

where $R'_1$, $R'_2$, $R'_3$ and $R'_7$ represent H or carbon chains, substituted or not, cyclic or not, aromatic or not, which may contain heteroatoms.

The α-ketoaldehyde involved in this reaction should preferably be methylglyoxal, ethylglyoxal, benzylglyoxal or a mixture of two of these α-ketoaldehydes. In the case of a mixture, the 2 distinct α-ketoaldehydes are added into the reaction mixture simultaneously or sequentially.

The molecule on which the 2 α-ketoaldehyde molecules condense should preferably be a nucleic base (adenine or cytosine) or its derivatives (substituted, such as 9-propyladenine, 1-propylcytosine or polyA), 2-aminopyridine or its derivatives (substituted, 2-amino-3-hydroxypyridine, aminopyrazine or 1-aminoisoquinoline), 2-aminobenzothiazole or benzamidine.

Preferably, the new adducts according to the invention should have the following formula:

| α-ketoaldehyde + X (diazotized derivatives whose N atoms are separated by a C atom, or amidines in the widest sense of the term) | Adducts (compounds of bis-addition of aldehyde, or cyclic α-iminoacids) of X: |
|---|---|
| methylglyoxal + 2-amino-3-methylpyridine (R = CH3) or 2-amino-3-hydroxypyridine (R = OH) | 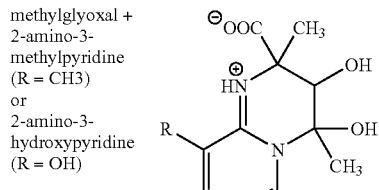 where R = CH3 or OH |
| methylglyoxal + 9-allyladenine | 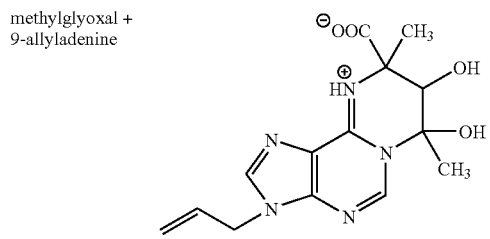 |
| α-ketoaldehyde + X (diazotized derivatives whose N atoms are separated by a C atom, or amidines in the widest sense of the term) | Adducts (compounds of bis-addition of aldehyde, or cyclic α-iminoacids) of X: |
|---|---|
| methylglyoxal + 9-butyladenine | |
| methylglyoxal + 9-(3-phenyl propyl)adenine | |
| methylglyoxal + 1-propylcytosine | |
| methylglyoxal + 1-amino-isoquinoline | |
| methylglyoxal + aminopyrazine | |

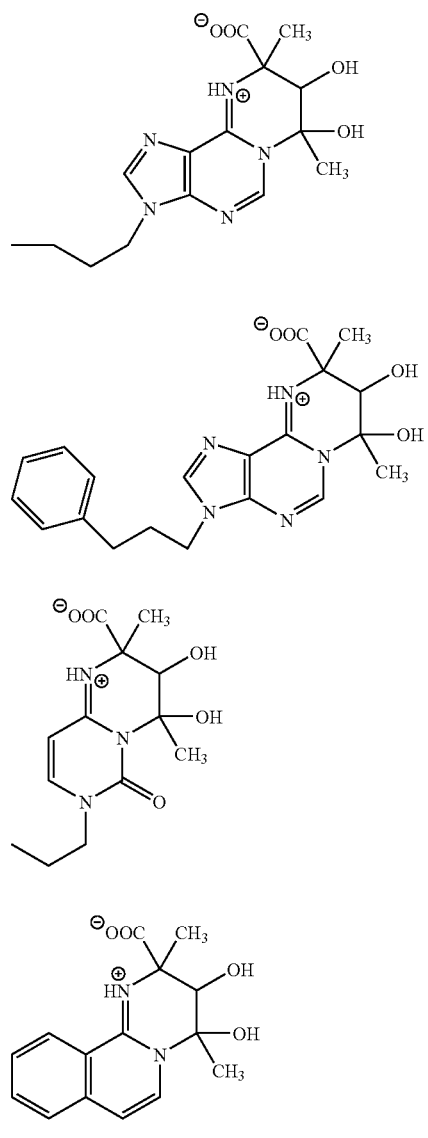

| -continued | |
|---|---|
| α-ketoaldehyde + X (diazotized derivatives whose N atoms are separated by a C atom, or amidines in the widest sense of the term) | Adducts (compounds of bis-addition of aldehyde, or cyclic α-iminoacids) of X: |
| methylglyoxal + 2-amino-benzothiazole | 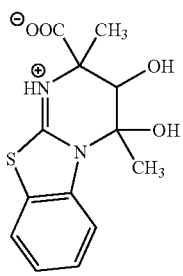 |
| methylglyoxal + benzamidine | 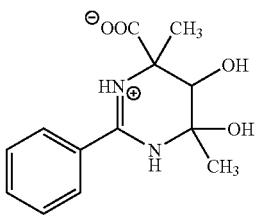 |
| methylglyoxal + 2-amino-perimidine | 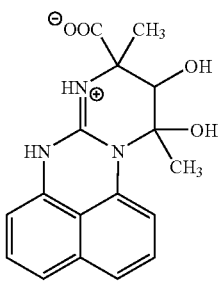 |
| ethylglyoxal + 2-amino-pyridine | 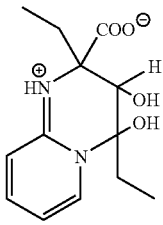 |

For all of these molecules, known or new, it should be pointed out that the hydroxyl functions borne on the sugars (for example, in the case of adenosine or 2'-deoxyadenosine adducts) may be modified, notably by acetylation.

As an example, the pKa for the product for reaction between methylglyoxal and 2-aminopyridine has been evaluated by the Applicants in an aqueous solution at 25° C.: it is approximately 2 for the carboxylic acid function and approximately 10 for the imine function, which confirms the zwitterionic character of the molecule at physiological pH.

During this reaction, the formation of four stereoisomers is observed, which are separable in the form of two mixtures of enantiomers, when the initial aminated derivative is not chiral. If it is chiral, four diastereoisomers are formed and may be isolated in the form of two mixtures.

The Applicants have demonstrated that, in the case of the adducts tested, i.e. those of 9-propyladenine, adenine and 1-propylcytosine, the biological activity of each separated diastereoisomer (in the form of two enantiomer mixtures) compared to those of their mixture was basically the same.

Advantageously, the molecules used in the context of the invention for their activity on the CFTR channels are the adducts obtained from 2 molecules of methylglyoxal and 2-amino-3-hydroxypyridine, or adenine, or 2'-deoxyadenosine, or 9-allyladenine, or 9-propyladenine, or 1-propylcytosine or 1-aminoisoquinoline. The adduct between ethylglyoxal and 2-aminopyridine is also preferred.

More generally, the invention concerns all the adducts generated by this reaction, except for those already described in Routabou et al. and Oya et al., as well as the use of all of these molecules as medicinal products.

The first therapeutic use of these molecules involves their use in a pharmaceutical formula that includes them as active principles.

In the entire application, a pharmaceutical formula is taken to mean a formula containing, as active principle(s), at least one molecule according to the invention in combination with a physiologically acceptable vehicle.

A pharmaceutical formula according to the invention may be administered orally (compressed tablets or hard gelatine capsules), parenterally (intravenously, intramuscularly subcutaneously) or via the breathing tract.

Pharmaceutical formulas according to the invention are furthermore characterised in that they contain quantities of active principle(s) that are suited to the dosage regimen, notably the mass of patients and the number of doses taken.

A second series of molecules is obtained from this first family of molecules through a new reaction demonstrated by the Applicants.

These new molecules are derivatives which come in the form of a zwitterion at physiological pH with the general formula:

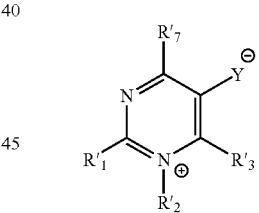

where $R'_1$ and $R'_2$ represent: —, H, or carbon chains, substituted or not, which may contain heteroatoms and which may form an aromatic or non-aromatic ring;

$R'_3$ and $R'_7$ represent: H, or carbon chains, substituted or not, which may contain heteroatoms;

Y=O or S.

The positive charge is borne by a tetravalent nitrogen atom, while the negative charge is linked to the deprotonated hydroxyl (phenol function) or thiol function.

As already mentioned, the molecules of the first family are obtained by the condensation of 2 α-ketoaldehyde molecules possessing enolisable hydrogen atoms on a molecule with two nitrogen atoms separated by a carbon which are able to react with α-ketoaldehyde, in the presence of $H_2O$ and/or an organic solvent such as ethanol, at a pH of 1 to 10 and a temperature between 25° C. and 80° C., giving rise to an α-iminoacid:

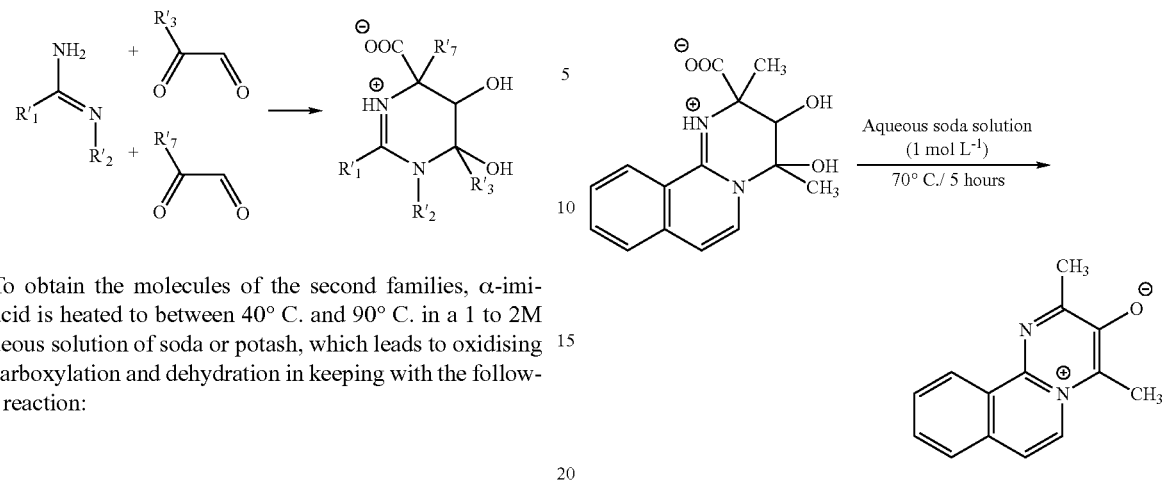

To obtain the molecules of the second families, α-iminoacid is heated to between 40° C. and 90° C. in a 1 to 2M aqueous solution of soda or potash, which leads to oxidising decarboxylation and dehydration in keeping with the following reaction:

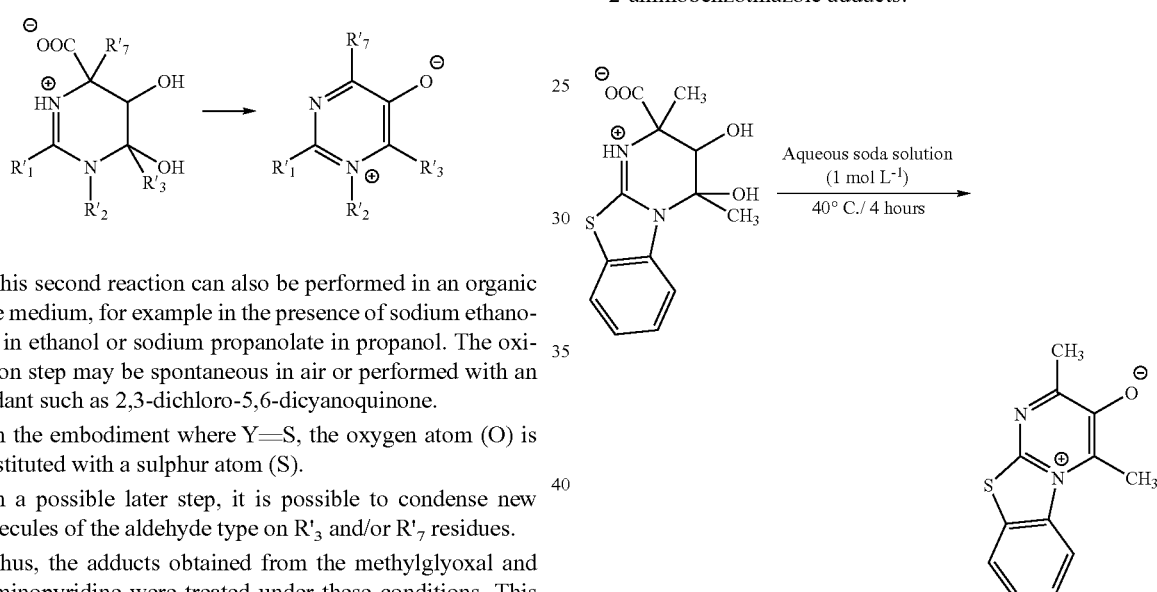

This second reaction can also be performed in an organic base medium, for example in the presence of sodium ethanolate in ethanol or sodium propanolate in propanol. The oxidation step may be spontaneous in air or performed with an oxidant such as 2,3-dichloro-5,6-dicyanoquinone.

In the embodiment where Y=S, the oxygen atom (O) is substituted with a sulphur atom (S).

In a possible later step, it is possible to condense new molecules of the aldehyde type on R'$_3$ and/or R'$_7$ residues.

Thus, the adducts obtained from the methylglyoxal and 2-aminopyridine were treated under these conditions. This reaction gave rise to the formation of the following derivative:

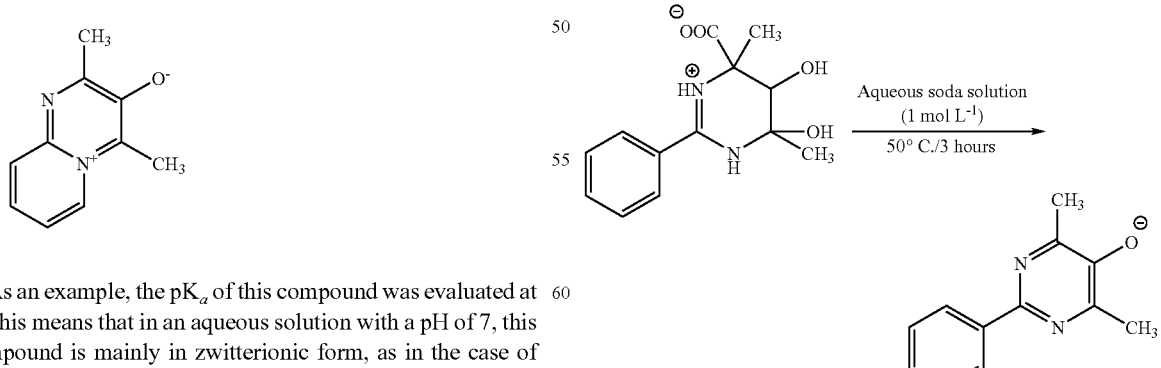

As an example, the pK$_a$ of this compound was evaluated at 4. This means that in an aqueous solution with a pH of 7, this compound is mainly in zwitterionic form, as in the case of highly diluted solutions such as those used for biological tests.

This reaction, although not complete, also takes place with, for example:

1-aminoisoquinoline adducts:

2-aminobenzothiazole adducts:

benzamidine adducts:

Starting with these compounds, it is possible to obtain a new series of molecules:

by substituting the oxygen atom (O) with a sulphur atom (S), giving rise to a sulphur compound. This reaction is exemplified below:

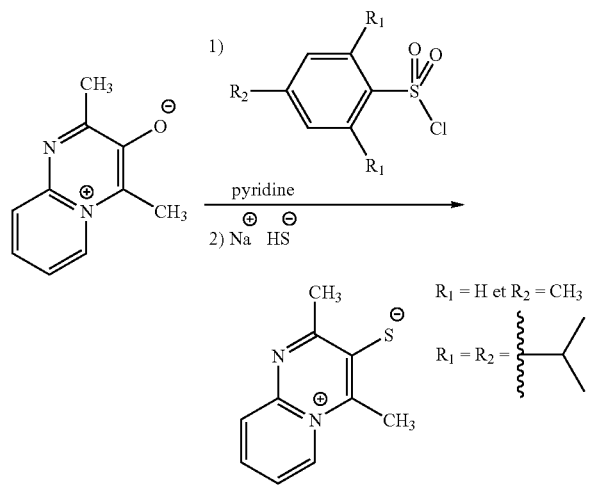

This transformation occurs in two steps: sulphonylation on the oxygen atom then substitution of the arylsulphonyl group by reaction with a hydrogen sulphide ion.

and/or by condensation on the level of the —CH3 groups located on either side of the hydroxyl group, with formaldehyde for example:

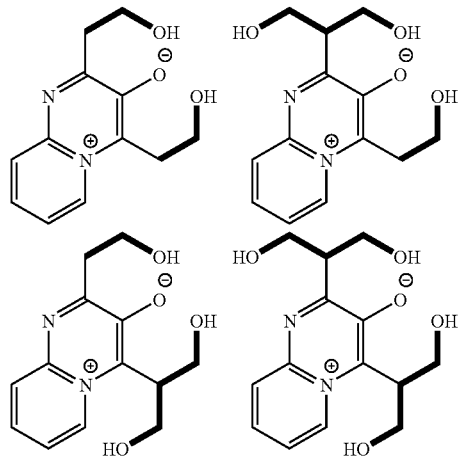

The hydrogen atoms of the methyl groups are indeed acids and can be substituted by reaction with electrophiles in a base medium.

Thus, an equivalent reaction can be produced with benzaldehyde, for example:

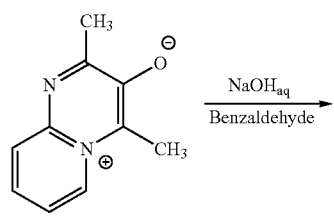

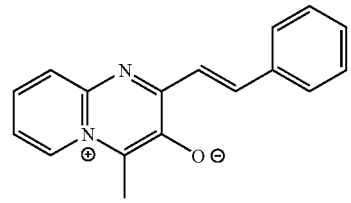

The reaction (condensation and dehydration) is performed in darkness, dissolving the oxygenated derivative in an aqueous 2M soda solution, then adding benzaldehyde (or a derivative) in slight excess. The pure derivative sought is obtained in the form of a red powder after silica column chromatography, eluting with a dichloromethane-methanol mixture. The reaction can be carried out in the presence of a large excess of benzaldehyde or a derivative, to make the second methyl group react in a similar manner and to obtain the disubstituted derivative.

A molecule with the following formula was thus obtained:

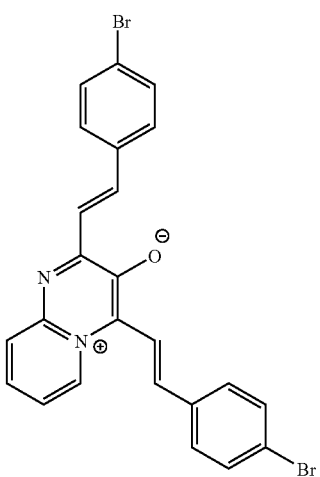

Beyond being new, the Applicants have demonstrated that the molecules which come in the form of a zwitterion at physiological pH, with the general formula:

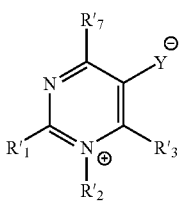

where $R'_1$, $R'_2$, $R'_3$ and $R'_7$ represent: —, H, or carbon chains, substituted or not, which may contain heteroatoms;

$R'_1$ and $R'_2$ may form an aromatic or non-aromatic ring;

Y=O or S, were susceptible to have therapeutic applications, notably in the preparation of medicinal products for treating diseases related to CFTR channel dysfunction.

Advantageously, in this last therapeutic application, the molecules of this second family have a formula chosen from the group including:

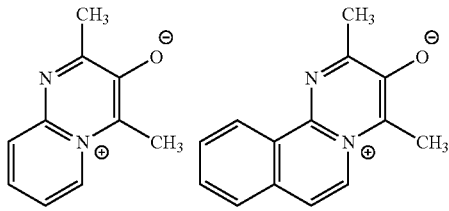

Lastly, there is a certain number of molecules already known as such and which come in the form of a zwitterion with the formula claimed at physiological pH, susceptible to have biological activity according to the invention.

One molecule meeting this definition is 7-methylguanosine, described, among others, in the Ermolinsky et al. document [Ermolinsky, B., Efimtseva, E., Alexeev, C., Mikhailov, S., Balzarini, J., and De Clercq, E. (2003). Dinucleoside Monophosphates containing AZT and 1 methyladenosine or 7-methylguanosine. Nucleosides, Nucleotides and Nucleic Acids 22(5-8), 853-855]:

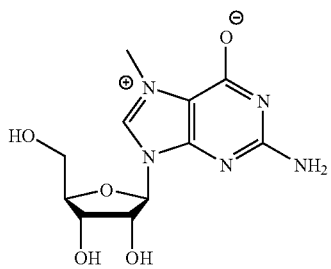

Here again, the hydroxyl functions borne by the sugars can be modified, notably by acetylation.

So far as the Applicants know, the molecules meeting such a definition have never been described within the context relating to therapeutic applications. Such molecules, used as medicinal products, notably in treating diseases related to CFTR channel dysfunction, are thus part of the invention.

Therefore, in one embodiment, the present invention is directed to a method of treating a disorder selected from cystic fibrosis, bronchial restricting diseases (such as asthma), and diarrhea, comprising administering a therapeutically effective amount of a compound of Formula I, II, III, IV, V, or VI:

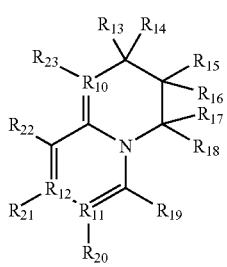
(I)

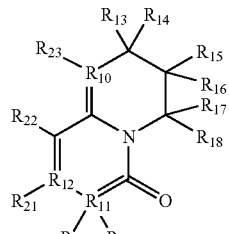
(II)

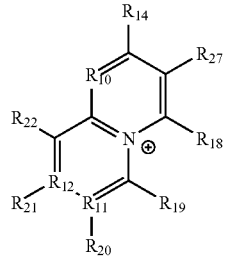
(III)

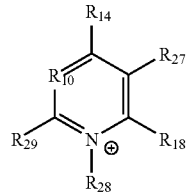
(IV)

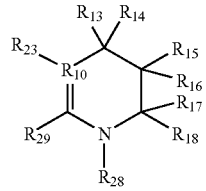
(V)

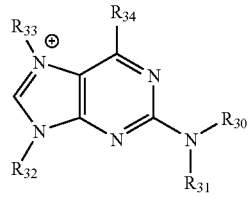
(VI)

or a salt thereof, wherein:
$R_{10}$ is chosen from N and P;
$R_{11}$ is chosen from C and N;
$R_{12}$ is chosen from C and N;
$R_{13}$ is chosen from COOH and COO$^-$;
$R_{14}$ is chosen from —H and —$C_1$-$C_6$ alkyl;
$R_{15}$ is chosen from —H, —OH, and —$C_1$-$C_6$ alkyl;
$R_{16}$ is chosen from —H and —$C_1$-$C_6$ alkyl;
$R_{17}$ is chosen from —H, —OH, and —$C_1$-$C_6$ alkyl;
$R_{18}$ is chosen from —H and —$C_1$-$C_6$ alkyl;
$R_{19}$ is chosen from —H and —$C_1$-$C_6$ alkyl;
$R_{20}$ is chosen from —H and —$C_1$-$C_6$ alkyl when $R_{11}$ is C, or $R_{20}$ is not present when $R_{11}$ is N;
$R_{21}$ is chosen from —H, —OH, and —$C_1$-$C_6$ alkyl when $R_{12}$ is C, or $R_{21}$ is not present when $R_{12}$ is N;
$R_{22}$ is chosen from —H, —OH, and —$C_1$-$C_6$ alkyl;
or $R_{21}$ and $R_{22}$, when $R_{12}$ is C, together with atoms to which they are bonded, form a 5 or 6 atom cycle or heterocycle where the cycle or the heterocycle may be substituted at one or more atoms by substituents chosen from —$C_1$-$C_6$ alkyl, —$C_1$-$C_6$ alkenyl, aryl, arylalkyl, heteroaryl, heteroarylalkyl, and $R_{24}$;

$R_{24}$ is a sugar moiety wherein $R_{24}$ includes:

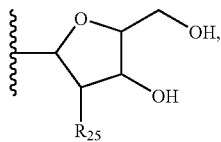

wherein $R_{25}$ is chosen from —H and —OH;

$R_{23}$ is not present or $R_{23}$ is —H and $R_{10}$ is cationic;

$R_{26}$ is chosen from —H and —$C_1$-$C_6$ alkyl, or $R_{26}$ is not present when $R_{11}$ is N;

$R_{27}$ is chosen from —OH, —$O^-$, —SH, and —$S^-$;

$R_{28}$ is chosen from —H, —OH, —$C_1$-$C_6$ alkyl, aryl, and heteroaryl;

$R_{29}$ is chosen from —H, —OH, —$C_1$-$C_6$ alkyl, aryl, and heteroaryl;

or $R_{28}$ and $R_{29}$, together with atoms to which they are bonded, form a mono-, bi-, or tri-heterocycle having one or more hetero atoms selected from N, S, and O, wherein such heterocycle may be substituted at one or more atoms by a substituent selected from —$C_1$-$C_6$ alkyl, $C_1$-$C_6$ alkenyl, aryl, arylalkyl, heteroaryl, heteroarylalkyl, or $R_{24}$;

$R_{30}$ is chosen from —H and —$C_1$-$C_6$ alkyl;

$R_{31}$ is chosen from —H and —$C_1$-$C_6$ alkyl;

$R_{32}$ is a sugar moiety wherein $R_{32}$ includes:

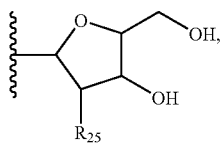

wherein $R_{25}$ is chosen from —H and —OH;

$R_{33}$ is chosen from —H and —$C_1$-$C_6$ alkyl; and $R_{34}$ is chosen from —OH, —$O^-$, —SH, and —$S^-$.

In another embodiment, the invention is directed to a compound, or a salt thereof, represented by Formula I, II, III, IV, V, or VI:

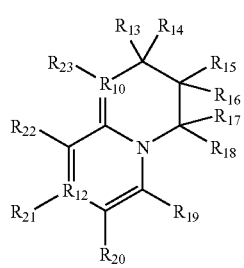

(I)

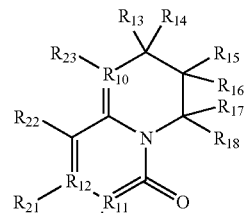

(II)

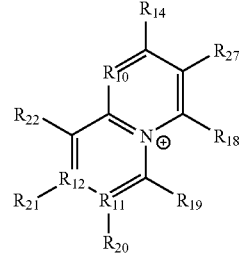

(III)

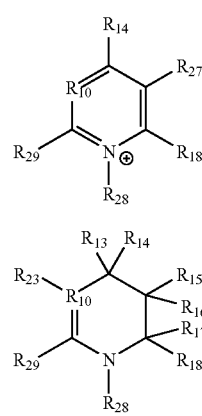

(IV)

(V)

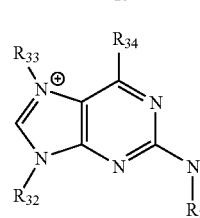

(VI)

wherein:

$R_{10}$ is chosen from N and P;

$R_{11}$ is chosen from C and N;

$R_{12}$ is chosen from C and N;

$R_{13}$ is chosen from COOH and $COO^-$;

$R_{14}$ is chosen from —H and —$C_1$-$C_6$ alkyl;

$R_{15}$ is chosen from —H, —OH, and —$C_1$-$C_6$ alkyl;

$R_{16}$ is chosen from —H and —$C_1$-$C_6$ alkyl;

$R_{17}$ is chosen from —H, —OH, and —$C_1$-$C_6$ alkyl;

$R_{18}$ is chosen from —H and —$C_1$-$C_6$ alkyl;

$R_{19}$ is chosen from —H and —$C_1$-$C_6$ alkyl;

$R_{20}$ is chosen from —H and —$C_1$-$C_6$ alkyl when $R_{11}$ is C, or $R_{20}$ is not present when $R_{11}$ is N;

$R_{21}$ is chosen from —H, —OH, and —$C_1$-$C_6$ alkyl when $R_{12}$ is C, or $R_{21}$ is not present when $R_{12}$ is N;

$R_{22}$ is chosen from —H, —OH, and —$C_1$-$C_6$ alkyl;

or $R_{21}$, and $R_{22}$, when $R_{12}$ is C, together with atoms to which they are bonded, form a 5 or 6 atom cycle or heterocycle where the cycle or the heterocycle may be substituted at one or more atoms by substituents chosen from —$C_1$-$C_6$ alkyl, —$C_1$-$C_6$ alkenyl, aryl, arylalkyl, heteroaryl, heteroarylalkyl, and $R_{24}$;
$R_{24}$ is a sugar moiety wherein $R_{24}$ includes:

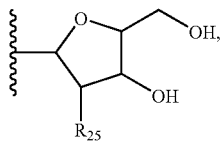

wherein $R_{25}$ is chosen from —H and —OH;
$R_{23}$ is not present or $R_{23}$ is —H and $R_{10}$ is cationic;
$R_{26}$ is chosen from —H and —$C_1$-$C_6$ alkyl, or $R_{26}$ is not present when $R_{11}$ is N;
$R_{27}$ is chosen from —OH, —O⁻, —SH, and —S⁻;
$R_{28}$ is chosen from —H, —OH, —$C_1$-$C_6$ alkyl, aryl, and heteroaryl;
$R_{29}$ is chosen from —H, —OH, —$C_1$-$C_6$ alkyl, aryl, and heteroaryl;
or $R_{28}$ and $R_{29}$, together with atoms to which they are bonded, form a mono-, bi-, or tri-heterocycle having one or more hetero atoms selected from N, S, and O, wherein such heterocycle may be substituted at one or more atoms by a substituent selected from —$C_1$-$C_6$ alkyl, $C_1$-$C_6$ alkenyl, aryl, arylalkyl, heteroaryl, heteroarylalkyl, or $R_{24}$;
$R_{30}$ is chosen from —H and —$C_1$-$C_6$ alkyl;
$R_{31}$ is chosen from —H and —$C_1$-$C_6$ alkyl;
$R_{32}$ is a sugar moiety wherein $R_{32}$ includes:

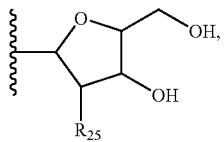

wherein $R_{25}$ is chosen from —H and —OH;
$R_{33}$ is chosen from —H and —$C_1$-$C_6$ alkyl; and
$R_{34}$ is chosen from —OH, —O⁻, —SH, and —S⁻;
with a proviso that, in compounds of Formula I, when $R_{11}$ and $R_{12}$ are C, and $R_{15}$ and $R_{17}$ are both —OH, then $R_{20}$, $R_{21}$, and $R_{22}$ are not —H; and
with an additional proviso that, in compounds of Formula I, when $R_{11}$ is N and $R_{12}$ is C, and when $R_{15}$ and $R_{17}$ are both —OH, then $R_{21}$ and $R_{22}$ together with atoms to which they are attached do not form the following structures:

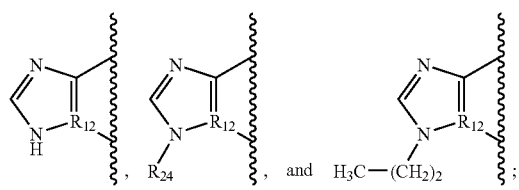

or, optionally, with an additional proviso that, in compounds of Formula I, when $R_{11}$ is N and $R_{12}$ is C, and when $R_{15}$ and $R_{17}$ are both —OH, then $R_{21}$ and $R_{22}$ together with atoms to which they are attached do not form the following structure:

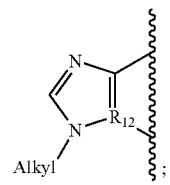

with an additional proviso that, in compounds of Formula II, when $R_{14}$ is —$CH_3$, $R_{15}$ is —OH, $R_{16}$ is —H, $R_{17}$ is —OH, $R_{18}$ is —$CH_3$, $R_{11}$ is N, $R_{12}$ is C, and $R_{20}$ is —H, then $R_2$, and $R_{22}$ are not —H; and
with an additional proviso that, in compounds of Formula V, when $R_{15}$ and $R_{17}$ are both —OH, then $R_{27}$ and $R_{28}$, together with atoms to which they are bonded, do not form the following structures:

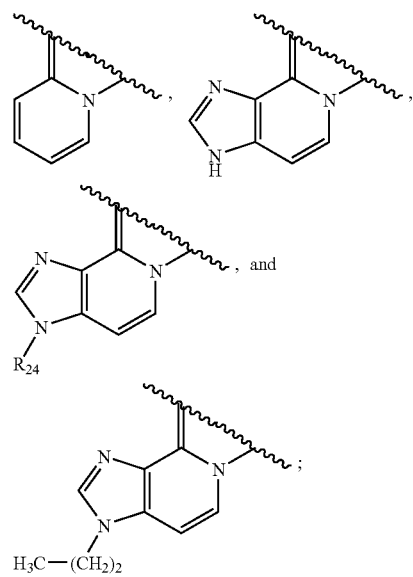

or, optionally, with an additional proviso that, in compounds of Formula V, when $R_{15}$ and $R_{17}$ are both —OH, then $R_{27}$ and $R_{28}$, together with atoms to which they are bonded, do not form the following structure:

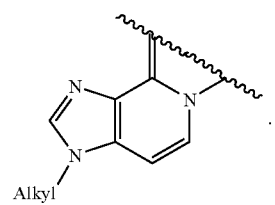

The advantages arising from the present invention are illustrated in the examples of embodiments presented below, backed up by the appended figures.

I. Equipment and Methods

1. Synthesis of the Compounds in Family I (Compounds 1 to 5 and 9 to 10):

a—General procedure: The principle behind this synthesis was essentially described in Routaboul et al. (2002) [7]. A 2-aminopyridine is dissolved in the commercial 40% methylglyoxal aqueous solution. The mixture is heated to 50° C. under argon. After evaporation under reduced pressure, the mixture of the two isomers is separated from the reaction medium by $C_{18}$ reverse phase cartridge chromatography, eluting with water. After evaporation of the solvent, the diastereoisomer mixture is dissolved in a minimum of methanol and precipitated in the anhydrous ether. For certain adducts, the diastereoisomers are separated by silica gel column chromatography (dry deposit; elution: $CH_2Cl_2$/MeOH gradient [9:1] to [7:3]). After evaporation of the solvent under reduced pressure, they are dissolved in water and purified by another round of $C_{18}$ reverse phase cartridge chromatography (eluant: water). The compounds come in the form of white powders.

b—Compound 1: 2'-deoxyadenosine Adducts

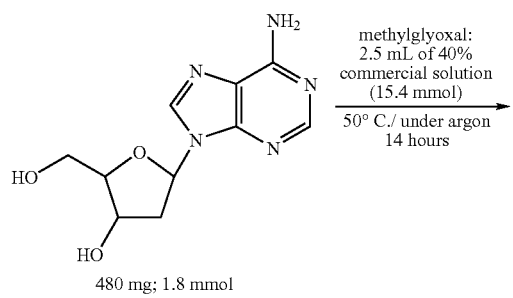

The reaction yield was 20% for the majority adduct (150 mg or 0.35 mmol) and 7% for the minority adduct (53 mg or 0.12 mmol).

c—Compound 2: 1-propylcytosine Adducts

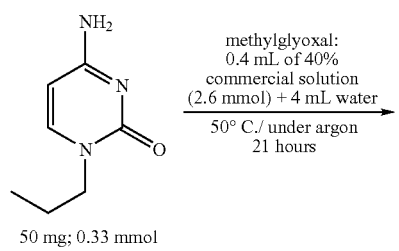

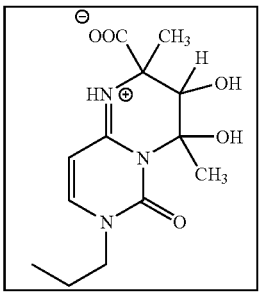

A mixture of diastereoisomer adducts was obtained with a 74% yield (73 mg or 0.25 mmol).

d—Compound 3: 2-amino-3-hydroxypyridine Adducts

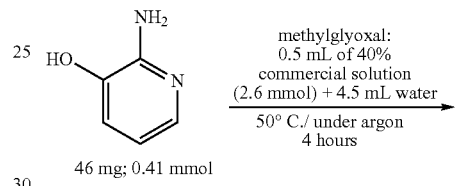

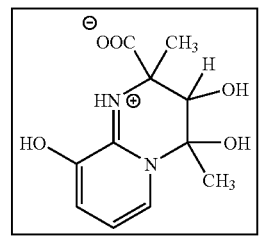

A mixture of diastereoisomer adducts was obtained with a 73% yield (77 mg or 0.30 mmol).

e—Compound 4: 1-aminoisoquinoline Adducts

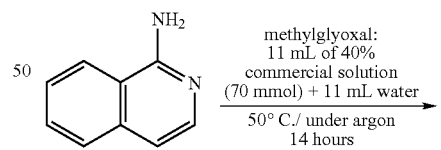

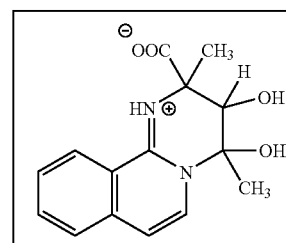

The mixture of diastereoisomer adducts is precipitated and is separated from the reaction medium by filtration and stripping with a minimum of anhydrous diethyl ether. It is obtained with a 82% yield (2.065 g or 7.2 mmol).

f—Compound 5: Adenine Adducts

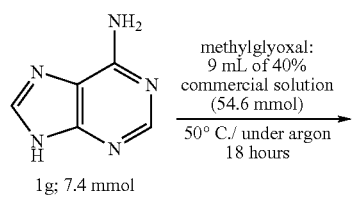

1g; 7.4 mmol

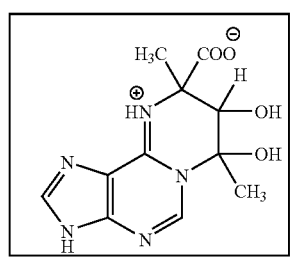

The reaction yield was 46% for the majority adduct (0.950 g or 3.4 mmol) and 20% for the minority adduct (0.413 g or 1.48 mmol).

g—Compound 9: 9-propyladenine Adducts

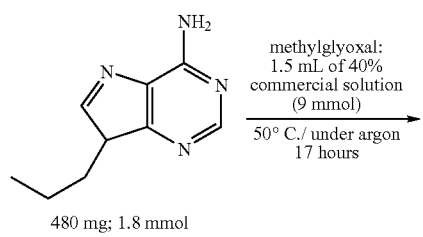

480 mg; 1.8 mmol

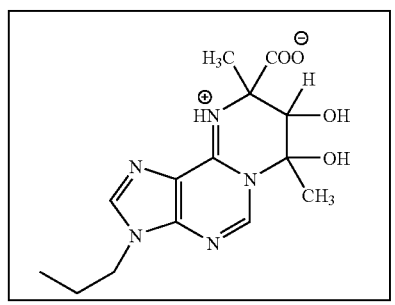

The reaction yield was 24% for the majority adduct (109 mg or 0.34 mmol) and 17% for the minority adduct (76 mg or 0.24 mmol).

h—Compound 10: 9-allyladenine Adducts

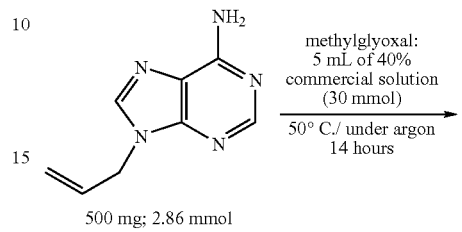

500 mg; 2.86 mmol

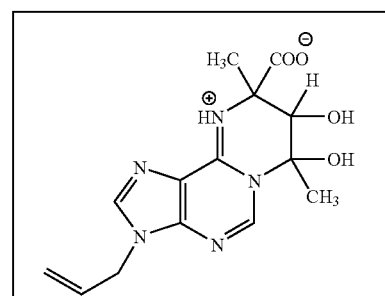

After separation from the reaction medium by $C_{18}$ reverse phase cartridge chromatography, the majority adduct is isolated and crystallised in propan-2-ol. This gives 390 mg or 1.22 mmol, for a 43% yield.

2. Synthesis of the Compounds in Family II (compounds 6 and 7):

a—General procedure: The compounds in family II are obtained using the compounds in family I, by heating in a base medium.

b—Compound 6: 2-aminopyridine Derivative $1^{st}$ Step: Synthesis of 2-aminopyridine Adducts

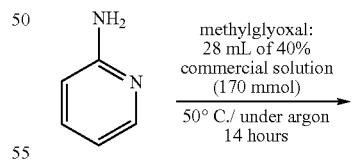

2 mg; 21 mmol

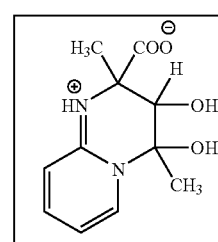

2nd Step: Synthesis of the 2-aminopyridine Derivative

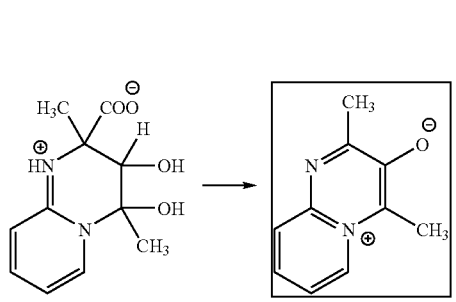

The mixture of diastereoisomers (200 mg, 0.84 mmol) in solution in soda (1 mol $L^{-1}$, 25 mL) is heated to 70° C. for 4.5 hours. After cooling, the solution is neutralised (pH 7.2) with a hydrochloric acid solution. The product is desalted by filtration on a $C_{18}$ reverse phase cartridge (eluant: water, then methanol) then purified by another round of $C_{18}$ reverse phase cartridge chromatography. After evaporation of the solvent, the product is obtained in the form of a yellow solid (119 mg; 0.68 mmol), with a 81% yield.

c—Compound 7: 1-aminoisoquinoline Derivative

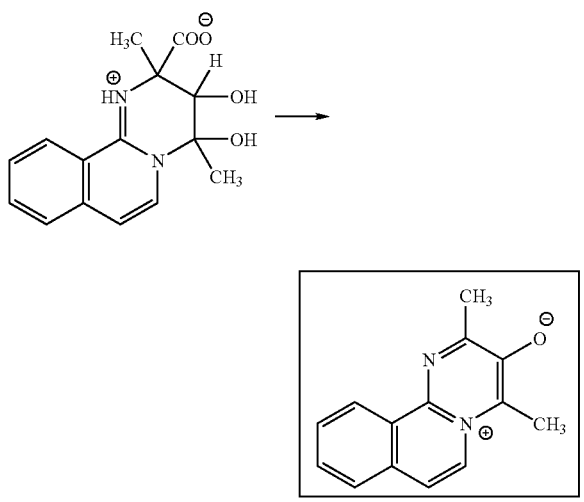

The mixture of diastereoisomers (150 mg, 0.52 mmol) described in section 1-e (compound 4), in solution in soda (1 mol $L^{-1}$, 2 mL), is heated to 70° C. for 5 hours. After cooling, the solution is neutralised (pH 7.2) with a phosphoric acid solution. After extraction with dichloromethane (3 times 10 mL) and evaporation of the solvent, the residue is chromatographed on a silica column (deposit: dichloromethane, elution: dichloromethane/methanol mixture). After evaporation of the solvent, two products are isolated: the expected derivative in the form of a yellow solid (8 mg, 0.04 mmol, 8%) and the 1-aminoisoquinoline (21 mg, 0.15 mmol, 28%) characterised by $^1$H NMR and $^{13}$C spectroscopy.

3. Obtaining Compound 8:

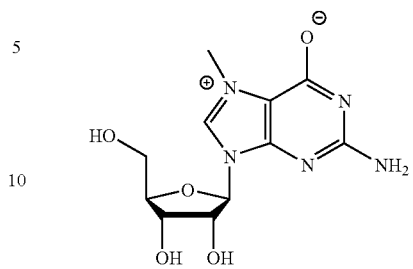

The information needed to obtain 7-methylguanosine is available in the Ermolinsky et al. document.

4. Cell cultures: CHO cells (Chinese Hamster Ovary cell line) have been stably transfected by a vector containing the wild-type CFTR receptor gene (CHO-WT) or a mutated receptor gene whose glycine residue in position 551 is substituted by aspartic acid (CHO-G551D). The cells were cultivated at 37° C. in the presence of 5% of $CO_2$ and maintained in MEM medium containing 7% foetal bovine serum, 0.5% antibiotics (50 IU/ml penicillin and 50 µg/ml streptomycin), as well as 100 µM or 20 µM methotrexate.

Experiments were also carried out on Calu-3 cells, a human lung cell line which naturally expresses the wild-type CFTR protein, cultivated as indicated above, and on CF15 cells, which are human nasal epithelial cells expressing the mutated F508-CFTR gene (deletion of a phenylalanine residue in position 508).

5. Biological activity of CFTR Channels: The activity of the chloride ion channels was evaluated by measuring the efflux of radioactive $^{125}I^-$ iodide coming out of the transfected CHO cells. All experiments were performed by a robotic system (Perkin Elmer Life Sciences, Courtaboeuf, France). The cells were cultivated in 24-well plates to perform parallel experiments and to carry out a comparative study. At the start of each experiment, the cells were stripped with an efflux buffer containing (in mM): 137 NaCl, 5.36 KCl, 0.8 $MgCl_2$, 5.5 glucose and 10 HEPES, pH 7.4. The cells are then incubated in an efflux buffer containing 1 µM KI and 1 µCi $Na^{125}I$/ml (NEN, Boston, Mass.) for 30 minutes at 37° C. to enable the $^{125}I$ to achieve equilibrium. The cells were then stripped with the efflux medium to remove the extracellular $^{125}I$. The loss of intracellular $^{125}I$ was determined by sampling medium with efflux buffer once a minute for 11 minutes. The first 4 aliquots were used to establish a stable base line in the efflux buffer alone. Residual radioactivity was extracted using 0.1N NaOH and determined using a Packard Cobra II gamma-ray counter (Perkin Elmer Life Sciences, Courtaboeuf, France). The results represent the mean ±the standard deviation (SD) of 4 independent experiments.

6. Cytotoxicity test: The MTT toxicity test is a colorimetric test based on the capacity of mitochondrial dehydrogenase to metabolise MTT (yellow tetrazolium salt) into formazan (purple). Absorbance, proportional to the concentration of colorant converted, can then be measured by spectrophotometry. The CHO cells are incubated in 96-well plates in the presence of the agent to be tested for 2 hours. Three checks are performed: 100% living cells: cells with agents; 0% living cells: cells left in the open air; white: medium without cells. The cells are rinsed with RPMI medium without phenol red so that the colour of the medium does not interfere with the absorbance measurements. Then they are incubated for 4 hours with 100 µl of RPMI solution supplemented with MTT (0.5mg/ml). The medium is then removed and 100 µl of DMSO are added to solubilise the converted colorant (formazan). Absorbance is measured by spectrophotometry at 570 nm (purple) and 630 nm (background noise). The following calculation is made to eliminate the background noise: $DO_{real}=DO_{570nm}-DO_{630nm}$. Then the results are normalised in relation to the controls (100% and 0% of living cells) and are presented in the form of the mean +/−SEM.

7. Addition of pharmacological agents: the molecules of the invention (compounds 1 to 10) and the already known CFTR channel activators (forskolin and genistein) were added at the concentrations indicated.

II. Results

1. Effects of the Tested Compounds on CFTR Receptor Activity:

The effect of the different synthesised compounds on CFTR chloride channel activity was tested on CHO cells overexpressing the wild-type receptor (CHO-WT). A 100% reference activation level was chosen for activation in the presence of 1 µM forskolin (Fsk). The components tested were added at a concentration of 1 µM. In case of a significant increase, the compound was listed as an activator. In case of activation significantly lower than 100% in the presence of the compound, this was listed as an inhibitor.

Examples of the diagram obtained are illustrated in FIG. 1.

To refine this study, the IC50 values for the inhibitors and the EC50 values for the activators were determined. The percentage of activation is monitored in the presence of increasing concentrations of the tested compound. For inhibitors, 100% activation was obtained in the presence of 5 µM forskolin. For activators, the percentage of activation was monitored in the presence of 1 µM forskolin.

Figure 2:
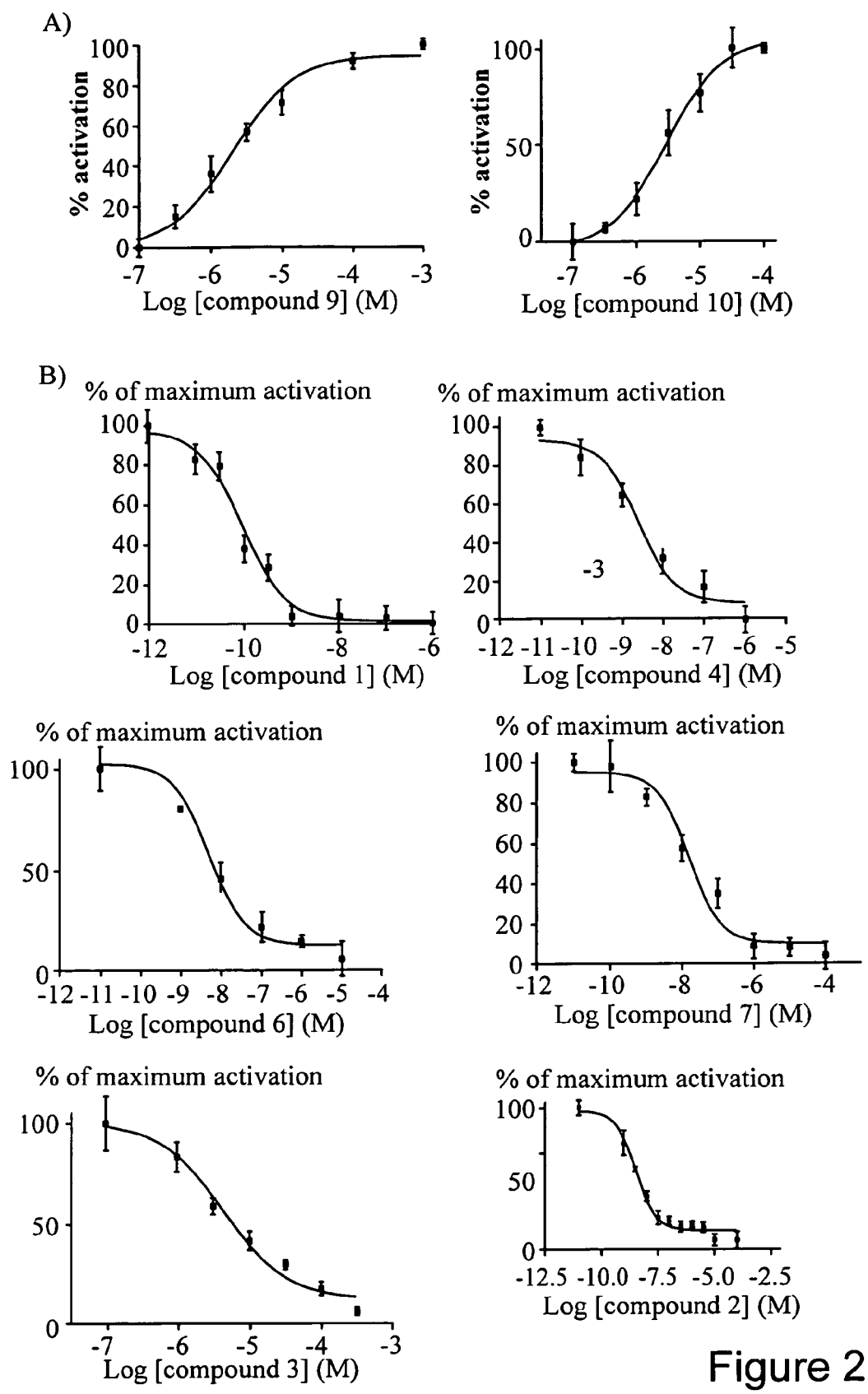
FIG. 2: Determination curves:
A) EC50's for the activator compounds (compounds 9 and 10), established in the presence of 1 μM of forskolin;
B) IC50's for the inhibitor compounds (compounds 1 to 4 and 6 to 7), established in the presence of 5 μM of forskolin.

Examples of effect/dose curves for determining the EC50 and IC50 values are illustrated in FIG. 2.

A study was carried out for the 11 compounds synthesised on 4 different cell lines (CHO-wt, CHO-G551D, Calu3 and CF15). Glibenclamide and betaine inhibitors were also included in this study. It should be pointed out that, for the effects on CF15 cells, the iodide ion flux was measured after 24 hours of incubation at 27° C. All measurements were made in the presence of 5 µm Fsk (CHO-wt and Calu-3) or 10 µm Fsk+30 µm genistein (G551D-CFTR and CF15). The derivatives tested were added directly in a solution while the glibenclamide control was incubated for 30 minutes before measuring the iodide ion flux. The results are presented in table I below:

| | | | IC50 or EC50 | | | |
| --- | --- | --- | --- | --- | --- | --- |
| Compound | Formula | Effect | CHO-WT cells | CHO-G551D | Calu3 human lung cells | CF15 cells |
| Glibenclamide | See page 4 | − | 15 µM | 8 µM | 12 µM | 12 µM |
| Betaine | | − | 96 µM | | | |
| 1 | | − | 71 pM | 43 nM | 93 pM | 68 pM |
| 2 (mixture of isomer 2a and isomer 2b) | | − | 2 nM | 154 nM | 2 nM | 6 nM |

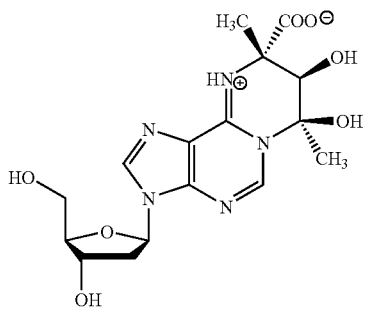

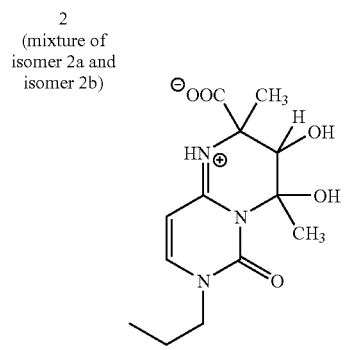

-continued

| Compound | Formula | Effect | IC50 or EC50 | | | |
|---|---|---|---|---|---|---|
| | | | CHO-WT cells | CHO-G551D | Calu3 human lung cells | CF15 cells |
| 2a (majority isomer) | | − | 2 nM | | | |
| 2b (minority isomer) | | − | 1.5 nM | | | |
| 3 (mixture of isomers) | | − | 4 μM | 36 μM | 11 μM | 7 μM |
| 4 (mixture of isomers) | | − | 2.5 nM | 190 nM | 16 nM | 9 nM |
| 4a (majority isomer) | | − | 3 nM | | | |
| 5 (mixture of isomer 5a and isomer 5b) | | − | 6 μM | 110 μM | 12 μM | 6 μM |

-continued

| Compound | Formula | Effect | IC50 or EC50 | | | |
|---|---|---|---|---|---|---|
| | | | CHO-WT cells | CHO-G551D | Calu3 human lung cells | CF15 cells |
| 5a (majority isomer) | | – | 10 µM | | | |
| 5b (minority isomer) | | – | 3 µM | | | |
| 6 | | – | 5 nM | 90 nM | 5 nM | 10 nM |
| 6 (chlorhydrate) | | – | 7 nM | | | |
| 7 | | – | 16 nM | 60 nM | 17 nM | 11 nM |
| 8 | | – | 3.5 µM | 15 µM | 11 µM | 11 µM |

-continued

| Compound | Formula | Effect | IC50 or EC50 | | | |
| --- | --- | --- | --- | --- | --- | --- |
| | | | CHO-WT cells | CHO-G551D | Calu3 human lung cells | CF15 cells |
| 9 (mixture of isomers) | | + | 2 μM | | | |
| 9a (majority isomer) | | + | 2 μM | | 2 μM | |
| 9b (minority isomer) | | + | 3 μM | | | |
| 10 (mixture of isomers) | | + | 7.5 μM | | | |
| 11 (mixture of isomers) | | − | 18 μM | | | |

The results show that the effects observed, both qualitatively and quantitatively, are preserved:
- between the cells expressing the wild-type receptor (Calu3) and cells overexpressing this same protein in an animal cell line (CHO-WT),
- for compound 9 of the first family, between the separated majority and minority adducts and the mixture of 2 diastereoisomers.

Moreover, it has been observed that most of the molecules have CFTR protein inhibitor activity. It should be pointed out that the inhibitor effect measured is usually much better than that of the inhibitors previously described in the literature. Likewise, the activators have a significant effect and could be used for their bronchodilator effect.

Lastly, parallel tests carried out on other ion channels have shown that these compounds have little or no activity on these channels (results not shown). Their action on the CFTR channels is therefore specific and targeted, thus providing therapeutic potential.

2. Effects of the Tested Compounds on Cell Viability:

The toxicity of the compounds with useful biological activity was tested. For this, CHO cells were incubated with said compounds for a duration of 2 to 24 hours at a concentration of 10 to 100 µM. Their toxicity was estimated by measuring cell viability, compared to that of cells without agents (100% of living cells) and that of cells left in open air (0% of living cells).

The results obtained for compounds 1 to 4, 6 to 7 and 9 to 10 of the invention (not shown) showed that they have no notable cytotoxicity, whatever the incubation duration and concentration used. Their therapeutic application can thus be fully envisaged.

3. Effects of the Tested Compounds on Mutated Receptors or in the Presence of Various Pharmacological Compounds:

In a more detailed study, the Applicants looked into the effects of an inhibitor (compound 1) or of an activator (compound 9), according to the invention, on the CFTR receptor:
- on a wild-type receptor (CHO-WT) or on a mutated receptor (CHO-G551D), encountered in certain forms of cystic fibrosis;
- in the presence of already known activators, such as forskolin, which increases the availability of cAMP involved in the activation of the regulator domain R, or genistein, which acts directly on the nucleotide binding domains and extends channel opening.

The results obtained are presented in Table II:

TABLE II

Effects of compound 1 and compound 9 on the activation of wild-type (CHO-WT) or mutated (CHO-G551D) CFTR, in the presence of various activators.

| Activator | Compound(s) added | CHO-WT | CHO-G551D |
|---|---|---|---|
| 1 µM Fsk | (activator) | activation | no effect |
| 1 µM Fsk | +1 µM compound 1 (inhibitor) | inhibition | no effect |
| 5 µM Fsk | +1 µM compound 1 (inhibitor) | inhibition | no effect |
| 1 µM Fsk | +1 µM compound 9 (activator) | activation (potentiation) | no effect |
| 10 µM Fsk + 30 µM genistein | | activation | activation |
| 10 µM Fsk + 30 µM genistein | +1 µM compound 1 (inhibitor) | inhibition | inhibition |
| 10 µM Fsk + 30 µM genistein | +1 µM compound 9 (activator) | activation | activation |

These experiments show that:
- compound 1 effectively antagonises the action of the forskolin and genistein activators, for wild-type receptors as well as mutated receptors;
- compound 9 has an activator effect on wild-type receptors but is unable to activate G551D mutated receptors. On the other hand, it can activate another mutated form of the receptor, ΔF508 (results not shown).

The invention claimed is:
1. A method of treating a disease or disorder selected from cystic fibrosis, asthma, and diarrhea, comprising administering a therapeutically effective amount of a compound of Formula I, II, III, IV, V, or VI, or a pharmaceutically acceptable salt thereof:

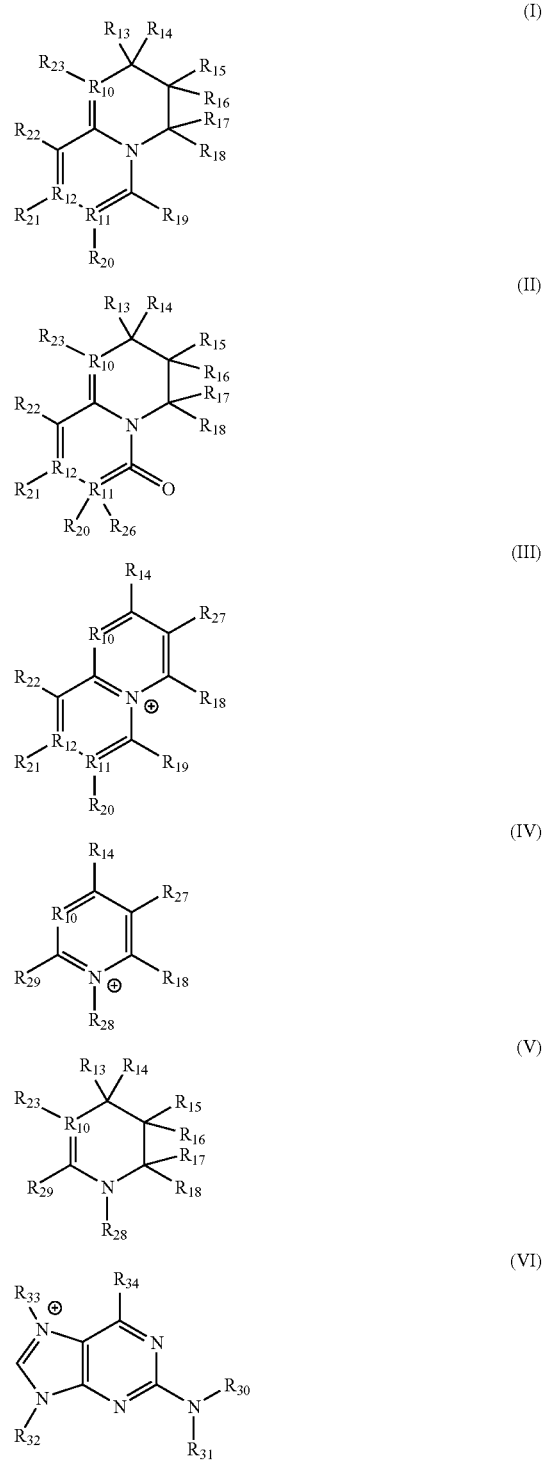

wherein:
$R_{10}$ is selected from the group consisting of N and P;
$R_{11}$ is selected from the group consisting of C and N;
$R_{12}$ is selected from the group consisting of C and N;

$R_{13}$ is selected from the group consisting of COOH and COO⁻;
$R_{14}$ is selected from the group consisting of —H and —$C_1$-$C_6$ alkyl;
$R_{15}$ is selected from the group consisting of —H, —OH, and —$C_1$-$C_6$ alkyl;
$R_{16}$ is selected from the group consisting of —H and —$C_1$-$C_6$ alkyl;
$R_{17}$ is selected from the group consisting of —H, —OH, and —$C_1$-$C_6$ alkyl;
$R_{18}$ is selected from the group consisting of —H and —$C_1$-$C_6$ alkyl;
$R_{19}$ is selected from the group consisting of —H and —$C_1$-$C_6$ alkyl;
$R_{20}$ is selected from the group consisting of —H and —$C_1$-$C_6$ alkyl when $R_{11}$ is C, or $R_{20}$ is not present when $R_{11}$ is N;
$R_{21}$ is selected from the group consisting of —H, —OH, and —$C_1$-$C_6$ alkyl when $R_{12}$ is C, or $R_{21}$ is not present when $R_{12}$ is N;
$R_{22}$ is selected from the group consisting of —H, —OH, and —$C_1$-$C_6$ alkyl;
or $R_{21}$ and $R_{22}$, when $R_{12}$ is C, together with atoms to which they are bonded, form a 5 or 6 atom cycle or heterocycle where the cycle or the heterocycle may be substituted at one or more atoms by substituents selected from the group consisting of —$C_1$-$C_6$ alkyl, —$C_1$-$C_6$ alkenyl, aryl, aryl($C_1$-$C_3$alkyl), heteroaryl, heteroaryl($C_1$-$C_3$alkyl), and $R_{24}$, wherein heteroaryl is selected from the group consisting of pyridine, pyridin-2-one, pyrimidine, furan, and thiophene;
$R_{24}$ is a sugar moiety having the structure:

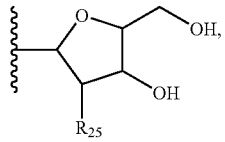

wherein $R_{25}$ is selected from the group consisting of —H and —OH;
$R_{23}$ is not present or $R_{23}$ is —H and $R_{10}$ is cationic;
$R_{26}$ is selected from the group consisting of —H and —$C_1$-$C_6$ alkyl;
$R_{27}$ is selected from the group consisting of —OH, —O⁻, —SH, and —S⁻;
$R_{28}$ is selected from the group consisting of —H, —OH, —$C_1$-$C_6$ alkyl, aryl, and heteroaryl, wherein heteroaryl is selected from the group consisting of pyridine, pyridin-2-one, pyrimidine, furan, and thiophene;
$R_{29}$ is selected from the group consisting of —H, —OH, —$C_1$-$C_6$ alkyl, aryl, and heteroaryl, wherein heteroaryl is selected from the group consisting of pyridine, pyridin-2-one, pyrimidine, furan, and thiophene;
or $R_{28}$ and $R_{29}$, together with atoms to which they are bonded, form a mono-, bi-, or tri-heterocycle having one or more hetero atoms selected from N, S, and O, wherein such heterocycle may be substituted at one or more atoms by a substituent selected from —$C_1$-$C_6$ alkyl, $C_1$-$C_6$ alkenyl, aryl, aryl($C_1$-$C_3$alkyl), heteroaryl, heteroaryl($C_1$-$C_3$alkyl), and $R_{24}$, wherein heteroaryl is selected from the group consisting of pyridine, pyridin-2-one, pyrimidine, furan, and thiophene;
$R_{30}$ is selected from the group consisting of —H and —$C_1$-$C_6$ alkyl;

$R_{31}$ is selected from the group consisting of —H and —$C_1$-$C_6$ alkyl;
$R_{32}$ is a sugar moiety having the structure:

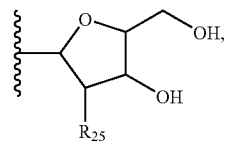

wherein $R_{25}$ is selected from the group consisting of —H and —OH;
$R_{33}$ is selected from the group consisting of —H and —$C_1$-$C_6$ alkyl; and
$R_{34}$ is selected from the group consisting of —OH, —O⁻, —SH, and —S⁻.

2. A method according to claim 1 wherein the compound is selected from the group consisting of:

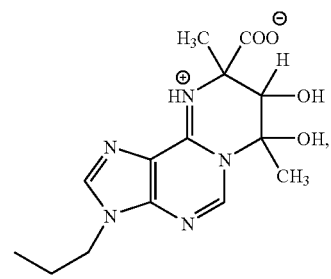

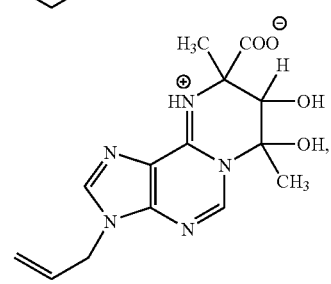

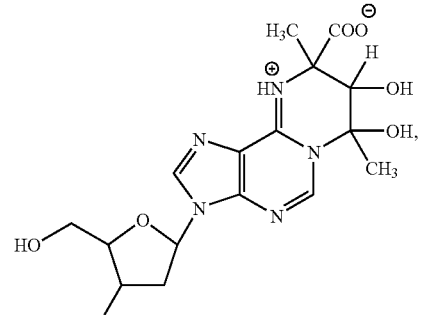

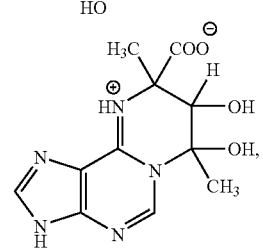

-continued

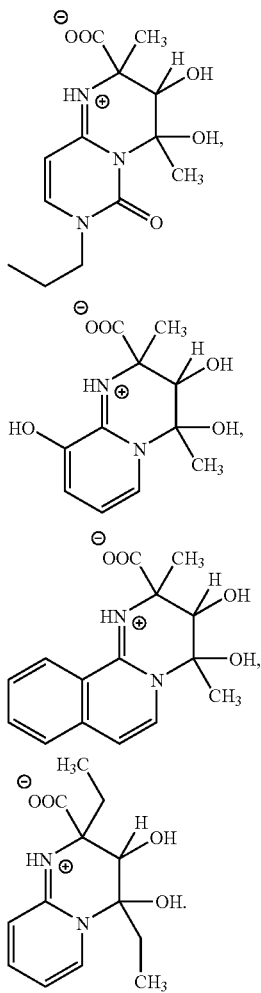

3. A method according to claim 1 wherein the compound is selected from the group consisting of:

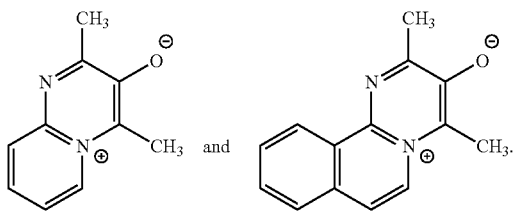

4. A method according to claim 1 wherein the compound is:

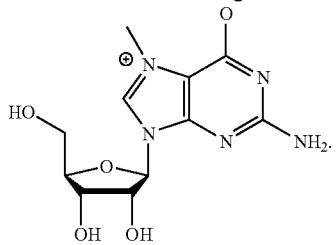

5. A compound, or a pharmaceutically acceptable salt thereof, represented by Formula I, II, III, IV, V, or VI:

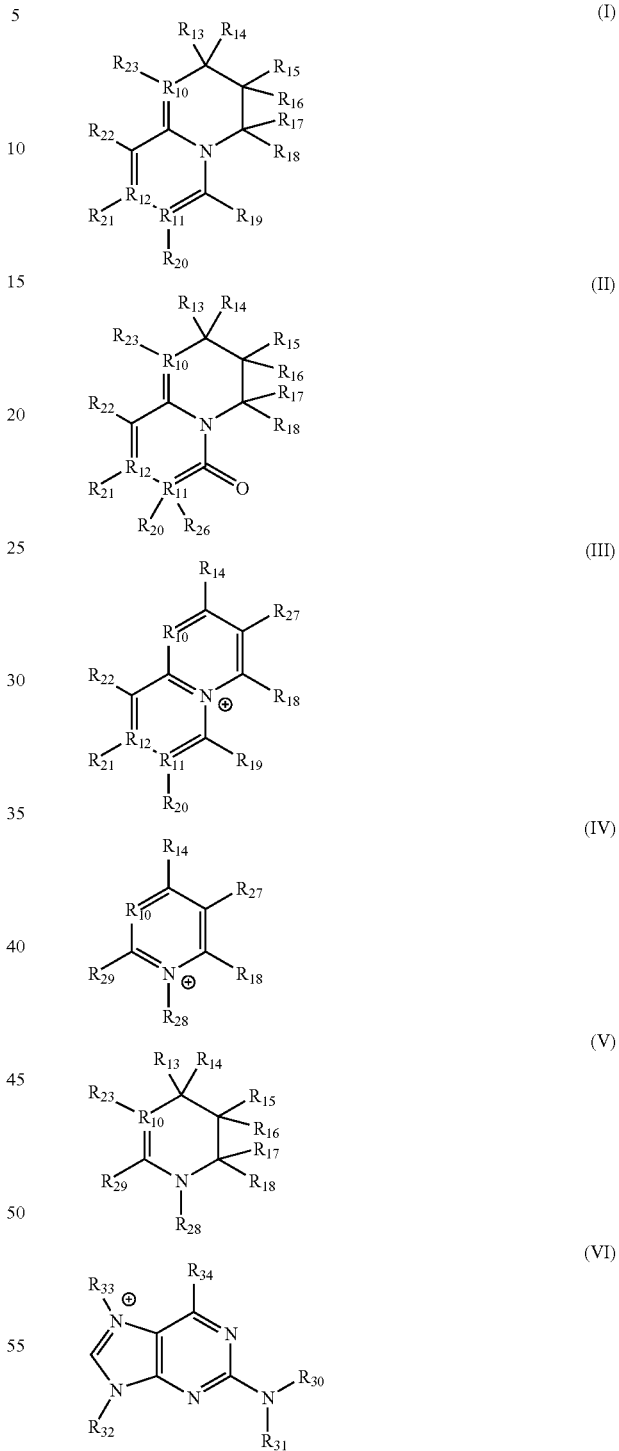

wherein
$R_{10}$ is selected from the group consisting of N and P;
$R_{11}$ is selected from the group consisting of C and N;
$R_{12}$ is selected from the group consisting of C and N;
$R_{13}$ is selected from the group consisting of COOH and COO$^-$;

$R_{14}$ is selected from the group consisting of —H and —C$_1$-C$_6$ alkyl;
$R_{15}$ is selected from the group consisting of —H, —OH, and —C$_1$-C$_6$ alkyl;
$R_{16}$ is selected from the group consisting of —H and —C$_1$-C$_6$ alkyl;
$R_{17}$ is selected from the group consisting of —H, —OH, and —C$_1$-C$_6$ alkyl;
$R_{18}$ is selected from the group consisting of —H and —C$_1$-C$_6$ alkyl;
$R_{19}$ is selected from the group consisting of —H and —C$_1$-C$_6$ alkyl;
$R_{20}$ is selected from the group consisting of —H and —C$_1$-C$_6$ alkyl when $R_{11}$ is C, or $R_{20}$ is not present when $R_{11}$ is N;
$R_{21}$ is selected from the group consisting of —H, —OH, and —C$_1$-C$_6$ alkyl when $R_{12}$ is C, or $R_{21}$ is not present when $R_{12}$ is N;
$R_{22}$ is selected from the group consisting of —H, —OH, and —C$_1$-C$_6$ alkyl;
or $R_{21}$ and $R_{22}$, when $R_{12}$ is C, together with atoms to which they are bonded, form a 5 or 6 atom cycle or heterocycle where the cycle or the heterocycle may be substituted at one or more atoms by substituents selected from the group consisting of —C$_1$-C$_6$ alkyl, —C$_1$-C$_6$ alkenyl, aryl, aryl(C$_1$-C$_3$alkyl), heteroaryl, heteroaryl(C$_1$-C$_3$alkyl, and $R_{24}$, wherein heteroaryl is selected from the group consisting of pyridine, pyridin-2-one, pyrimidine, furan, and thiophene;
$R_{24}$ is a sugar moiety having the structure:

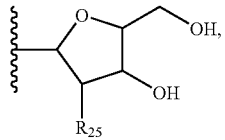

wherein $R_{25}$ is selected from the group consisting of —H and —OH;
$R_{23}$ is not present or $R_{23}$ is —H and $R_{10}$ is cationic;
$R_{26}$ is selected from the group consisting of —H and —C$_1$-C$_6$ alkyl;
$R_{27}$ is selected from the group consisting of —OH, —O$^-$, —SH, and —S$^-$;
$R_{28}$ is selected from the group consisting of —H, —OH, —C$_1$-C$_6$ alkyl, aryl, and heteroaryl, wherein heteroaryl is selected from the group consisting of pyridine, pyridin-2-one, pyrimidine, furan, and thiophene;
$R_{29}$ is selected from the group consisting of —H, —OH, —C$_1$-C$_6$ alkyl, aryl, and heteroaryl, wherein heteroaryl is selected from the group consisting of pyridine, pyridin-2-one, pyrimidine, furan, and thiophene;
or $R_{28}$ and $R_{29}$, together with atoms to which they are bonded, form a mono-, bi-, or tri-heterocycle having one or more hetero atoms selected from N, S, and O, wherein such heterocycle may be substituted at one or more atoms by a substituent selected from —C$_1$-C$_6$ alkyl, C$_1$-C$_6$ alkenyl, aryl, aryl(C$_1$-C$_3$alkyl), heteroaryl, heteroaryl(C$_1$-C$_3$alkyl), and $R_{24}$, wherein heteroaryl is selected from the group consisting of pyridine, pyridin-2-one, pyrimidine, furan, and thiophene;
$R_{30}$ is selected from the group consisting of —H and —C$_1$-C$_6$ alkyl;
$R_{31}$ is selected from the group consisting of —H and —C$_1$-C$_6$ alkyl;

$R_{32}$ is a sugar moiety having the structure:

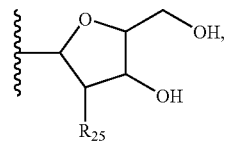

wherein $R_{25}$ is selected from the group consisting of —H and —OH;
$R_{33}$ is selected from the group consisting of —H and —C$_1$-C$_6$ alkyl; and
$R_{34}$ is selected from the group consisting of —OH, —O$^-$, —SH, and —S$^-$;
with a proviso that, in compounds of Formula I, when $R_{11}$ and $R_{12}$ are C, and $R_{15}$ and $R_{17}$ are both —OH, then $R_{20}$, $R_{21}$, and $R_{22}$ are not —H; and
with an additional proviso that, in compounds of Formula I, when $R_{11}$ is N and $R_{12}$ is C, and when $R_{15}$ and $R_{17}$ are both —OH, then $R_{21}$ and $R_{22}$ together with atoms to which they are attached do not form the following structures:

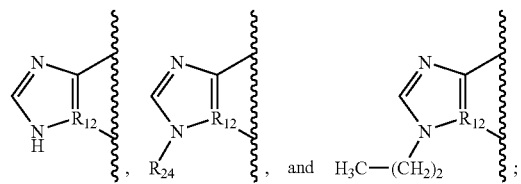

with an additional proviso that, in compounds of Formula II, when $R_{14}$ is —CH$_3$, $R_{15}$ is —OH, $R_{16}$ is —H, $R_{17}$ is —OH, $R_{18}$ is —CH$_3$, $R_{11}$ is N, $R_{12}$ is C, and $R_{26}$ is —H, then $R_{21}$ and $R_{22}$ are not —H; and
with an additional proviso that, in compounds of Formula V, when $R_{15}$ and $R_{17}$ are both —OH, then $R_{28}$ and $R_{29}$, together with atoms to which they are bonded, do not form the following structures:

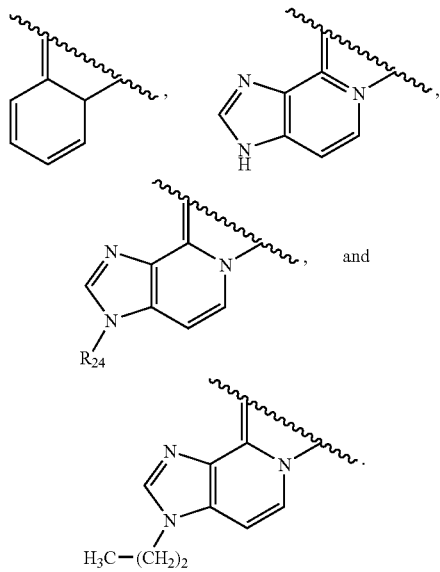

6. A compound, or a pharmaceutically acceptable salt thereof, according to claim 5, selected from:
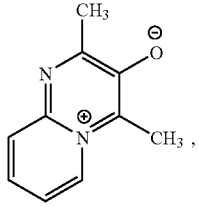 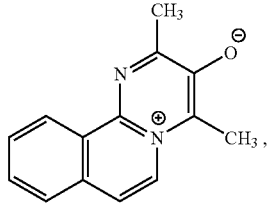
-continued
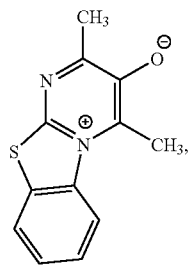 and 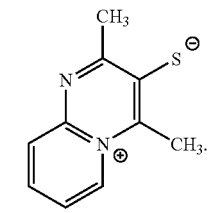
* * * * *